United States Patent [19]
Nishizawa et al.

[11] Patent Number: 5,615,954
[45] Date of Patent: Apr. 1, 1997

[54] APPARATUS FOR MEASURING THE DEW POINT OR FROST POINT OF A GAS HAVING LOW WATER CONTENT

[75] Inventors: Junichi Nishizawa, Miyagi-ken; Takahiko Kijima, Hyogo-ken, both of Japan; Edward F. Ezell, Warren, N.J.; Akira Makihara, Chiba-ken, Japan

[73] Assignee: Osaka Sanso Kogyo Ltd., Osaka, Japan

[21] Appl. No.: 360,441

[22] Filed: Dec. 21, 1994

Related U.S. Application Data

[62] Division of Ser. No. 286,395, Aug. 5, 1994, abandoned, which is a continuation of Ser. No. 992,447, filed as PCT/JP92/00492, Apr. 17, 1992, abandoned.

[30]    Foreign Application Priority Data

| Apr. 18, 1991 | [JP] | Japan | 3-86905 |
| Apr. 18, 1991 | [JP] | Japan | 3-86906 |
| Nov. 30, 1991 | [JP] | Japan | 3-357405 |
| Dec. 1, 1991 | [JP] | Japan | 3-357406 |
| Dec. 1, 1991 | [JP] | Japan | 3-357407 |

[51] Int. Cl.$^6$ .............. G01N 25/04; G01N 25/68; G01N 21/47; G01N 21/55
[52] U.S. Cl. .............. 374/17; 374/20; 73/29.01
[58] Field of Search .............. 374/17, 18, 19, 374/20, 27, 28; 73/335.01, 29.01

[56]    References Cited

U.S. PATENT DOCUMENTS

| 3,623,356 | 11/1971 | Bisberg . | |
| 4,045,971 | 9/1977 | Brenner, Jr. | 374/20 |
| 4,083,224 | 4/1978 | Gayst | 374/19 |
| 4,155,245 | 5/1979 | Coe . | |
| 4,216,669 | 8/1980 | Harding, Jr. . | |
| 4,335,597 | 6/1982 | Hayes, Jr. et al. | 374/20 |
| 4,629,333 | 12/1990 | Dosoretz et al. | 374/20 |
| 4,877,329 | 10/1989 | Sauerbaum et al. | 374/20 |
| 4,908,835 | 3/1990 | Nishiuchi et al. | 374/17 |
| 4,972,677 | 11/1990 | Moriya et al. . | |
| 5,052,818 | 10/1991 | Nishizawa et al. | 374/17 |

FOREIGN PATENT DOCUMENTS

| 345215 | 6/1989 | European Pat. Off. . |
| 409546 | 1/1991 | European Pat. Off. . |
| 0813208 | 3/1981 | U.S.S.R. . |
| 2028499 | 3/1980 | United Kingdom . |
| WO402291 | 12/1984 | WIPO . |

*Primary Examiner*—Diego F. F. Gutierrez
*Attorney, Agent, or Firm*—Roylance, Abrams, Berdo & Goodman, L.L.P.

[57]    ABSTRACT

The invention relates to an apparatus for determining the frost point of a gas containing a very small amount of water. The apparatus comprises (I) compartment A made of a good heat conductor; (II) an inlet for the gas to be measured, which inlet is provided on compartment A; and (III) a heater for adjusting the temperature in compartment A, and a temperature sensor. The apparatus further comprises (IV) compartment B which is adjacent to compartment A. At least part of compartment B is made of a poor heat conductor. Further, the apparatus comprises (V) a hole at the interface between compartments A and B and (VI) a reflector mirror having a temperature sensor. The reflector mirror is provided on compartment B in such a way as to cover the hole is connected thermally to a freeze source in such a way that the temperature of the reflector mirror can be varied from room temperature to at least −80° C. Also, the apparatus comprises (VII) a gas outlet provided on compartment B; (VIII) a small gap formed between the hole and the reflector mirror; (IX) a device that allows convergent rays of light or laser light to be emitted onto the surface of the reflector mirror; and (IX) a photodetector equipped with a condenser lens. The condenser lens condenses light from frost formed on the surface of the reflector mirror when said gas to be measured contacts said mirror and said water in said gas condenses as frost. Finally the apparatus comprises (XI) a detector device that senses the temperature at which frost occurs on the reflector mirror.

2 Claims, 26 Drawing Sheets

NUCLEUS FORMATION/SUBLIMATION
CYCLE TIME T(A2)(°C)

Fig. 7A
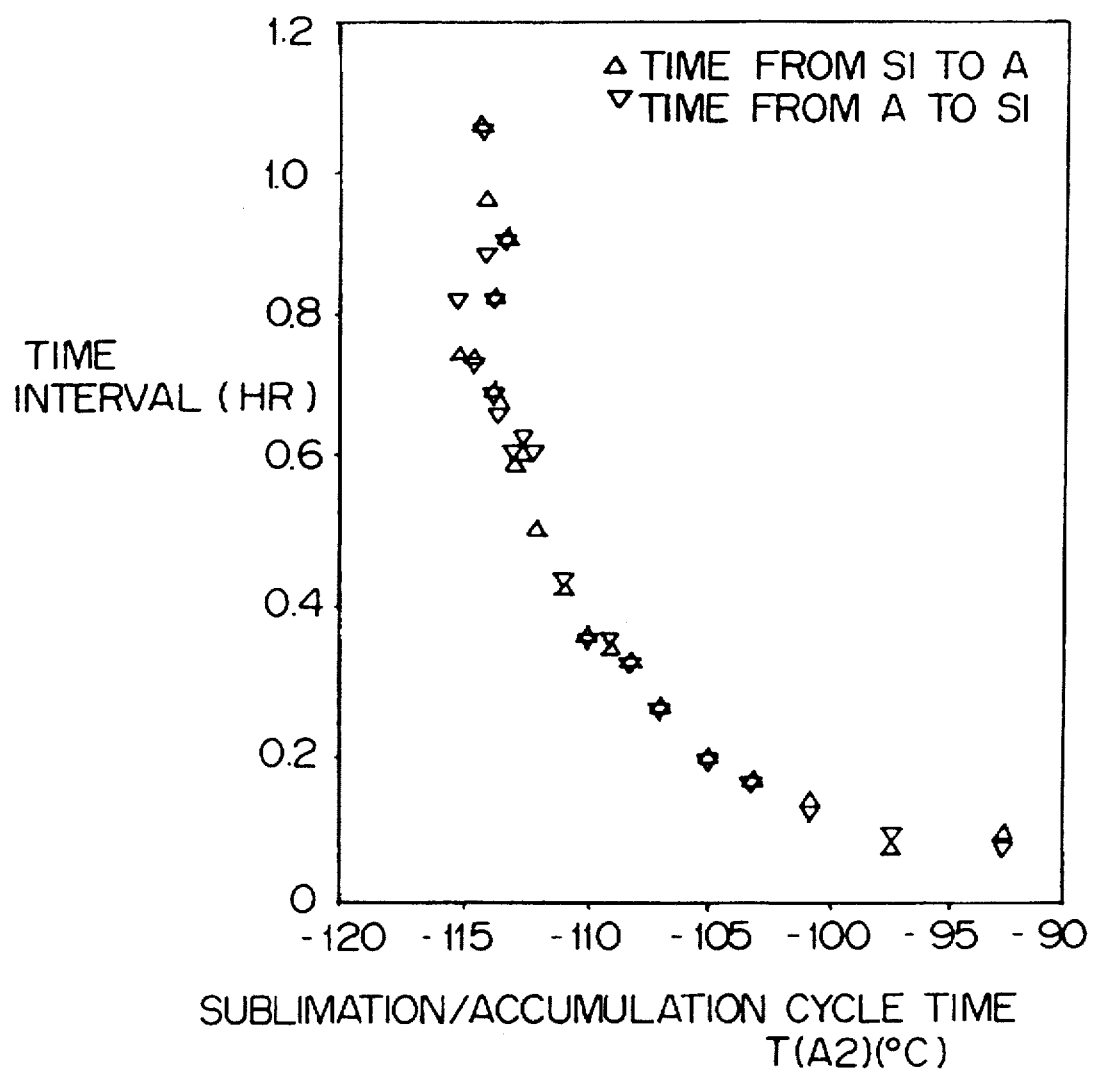
Fig. 7B

SCHEMATIC LAYOUT FOR THE SYSTEM OF TUBE CLEANUP SPEED MEASUREMENT

SCHEMATIC LAYOUT FOR GENERATION AND DILUTION OF STANDARD GAS OF LOW WATER CONTENT

APPARATUS FOR MEASURING THE DEW POINT OR FROST POINT OF A GAS HAVING LOW WATER CONTENT

This is a division of application Ser. No. 08/286,395 filed Aug. 5, 1994, now abandoned, which is a continuation of Ser. No. 992,447, filed as PCT/JP92/00492, Apr. 17, 1992, now abandoned.

FIELD OF THE INVENTION

The present invention enables the dew or frost point of a gas to be measured under the condition of an instantaneous equilibrium between the solid and vapor phases of water, thereby assuring that the measured dew or frost point corresponds to the saturation temperature of the gas while, at the same time, the vapor pressure of the gas corresponds to the saturation vapor pressure of ice at that temperature.

This invention relates to a method of measuring the dew or frost point of a gas having low water content and apparatus therefor.

BACKGROUND OF THE INVENTION

As has been pointed out in the references of many researchers, dictionaries and patents, it takes a very long time to measure dew or frost points, particularly low dew or frost points, and supercooling often takes place when the dew or frost point to be measured is −100° C. or below.

As a result of many repeated experiments, the present inventors have discovered a method that is believed to be the most accurate way of dew point and/or frost point measurement that is practical enough to be implemented with an industrially useful dew point or frost point meter.

It has been known to determine the water content of a gas by measuring its dew or frost point (see, for example, U.S. Pat. No. 5,052,818). In that method, the gas to be measured is blown against a reflecting mirror cooled to −80° C. or below and the condensation of dew or frost on the reflecting mirror is detected by a sudden increase in scattered light and the water content of the gas is determined from the dew or frost point. However, later studies of the present inventors have shown that below −90° C., the amount of condensation of dew or frost on the reflector mirror is so small that the detector sometimes fails to achieve the correct sensing of the point where such dew or frost condensation has occurred. Even if dew or frost condensation can be sensed by the detector, one often cannot be sure whether the sensed point of dew or frost condensation reflects the correct dew or frost point. In addition, if a phenomenon called "supercooling" occurs, dew or frost will not be condensed at the temperature where dew or frost condensation would otherwise occur. In this case, too, one is unable to know for sure whether the measured point reflects the correct dew or frost point.

SUMMARY OF THE INVENTION

As a result of extensive research efforts, the present inventors found that when the reflector mirror was held at a low temperature even after dew or frost condensation, thereby forming the solid phase of water in a suitable amount and when a heating, a cooling and a heating steps were conducted through at least one cycle, followed by detection of the temperature where the intensity of scattered light and/or reflected light was at a maximum or a minimum and the temperature where said intensity was at a minimum or a maximum, the two temperatures were almost the same and could be regarded as the correct dew or frost point. The present invention has been accomplished on the basis of this finding.

In its major aspect, the present invention relates to a method of determining the dew point or frost point of a gas containing a very small amount of water using an optical dew point meter including a reflector mirror the temperature of which can be varied from room temperature to any point of −80° C. or below, a means of contacting said reflector mirror with the gas to be measured, a means of irradiating said reflector mirror with focused rays of light and/or laser light, and a means of detecting the change in scattered light and/or reflected light due to the dew and/or frost condensed on said reflector mirror, said method comprising the steps of:

contacting said reflector mirror with the gas to be measured;

applying said focused rays of light and/or laser light onto that part of the reflector mirror where it is contacted with said gas;

gradually reducing the temperature of said reflector mirror, either before or while said reflector mirror and said gas contact, thereby condensing dew or frost on said reflector mirror; and gradually elevating the temperature of said reflector mirror to a point in the neighborhood of the dew or frost point but which is insufficient to have the dew or frost sublime completely from the mirror surface, thereby detecting the temperature at which the scattered light has a maximum intensity and/or the temperature at which the reflected light has a minimum intensity, or further cooling the reflector mirror to detect the temperature at which the scattered light has a minimum intensity and/or the temperature at which the reflected light has a maximum intensity, and designating said maximum and minimum temperatures as the dew or frost point of the gas of interest.

Preferably, the temperature of said reflector mirror is gradually reduced or elevated by cooling or heating said reflector mirror at a rate that is varied either stepwise or continuously generally along the curve represented by:

$$R(T) = R(T_0)[P'(T)/P'(T_0)]^n$$

where

T: the temperature (K) of the reflector mirror;

$T_0$: any specific temperature (K) that can be selected from the range of from room temperature to the temperature of liquid nitrogen;

R(T): the cooling and/or heating rate (K/min) at a selected temperature (K) of the reflector mirror;

P'(T): the derived function of the saturated vapor pressure of ice determined with the temperature (T) being taken as a variable;

$P'(T_0)$: a calculated value of the saturated vapor pressure of water at the specific temperature $T_0$; and n: the value so selected as to provide a substantially constant signal-to-noise ratio of at least 2 in the measurement of the change in reflected light and/or scattered light over a fixed temperature interval ΔT.

BRIEF DESCRIPTION OF THE DRAWINGS

FIGS. 7A and 7B are graphs showing the cycle times of the subliming point and the accumulation point as measured at low dew points (in the present invention);

DETAILED DESCRIPTION OF THE INVENTION

Figure 1:
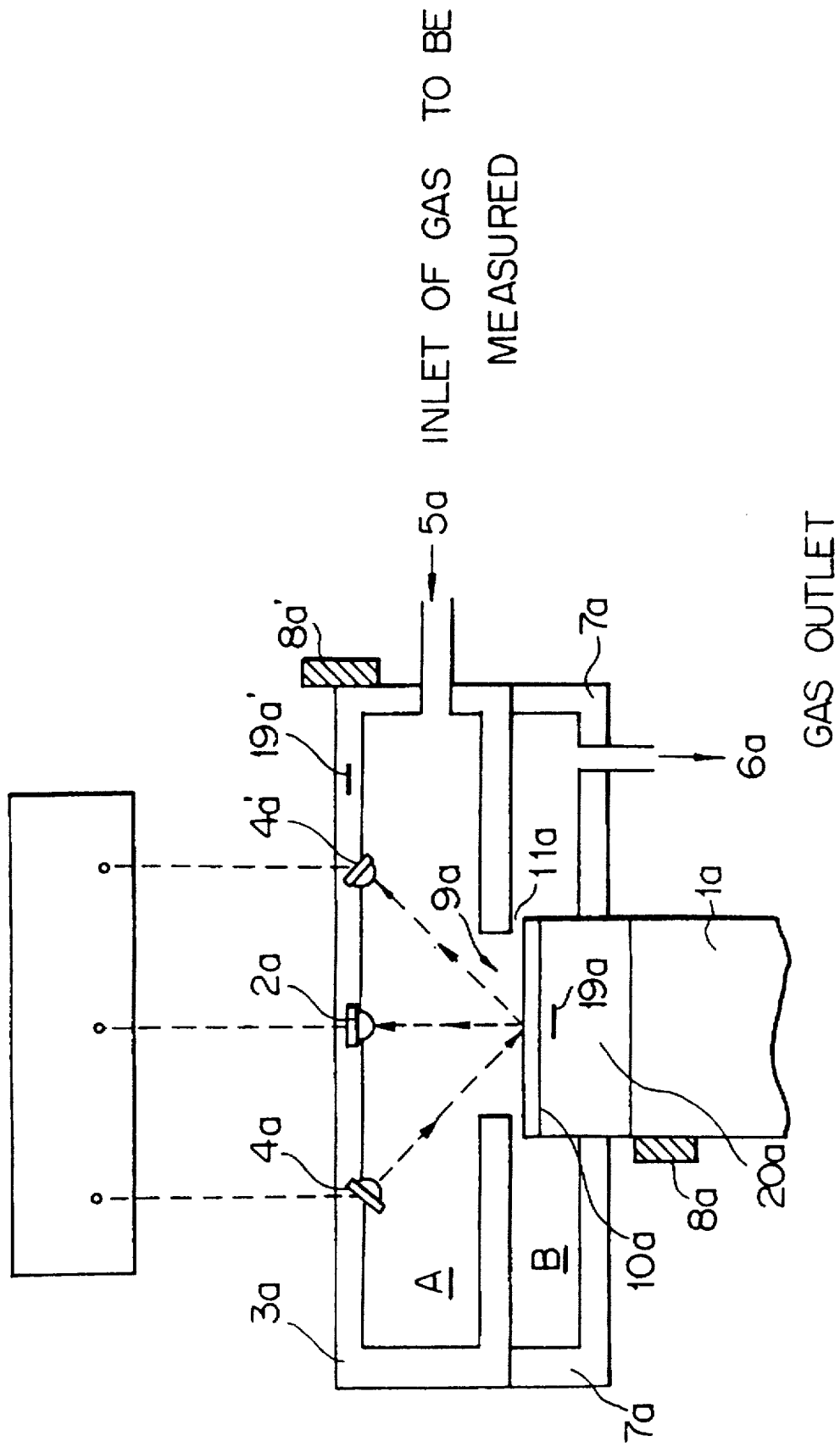
FIG. 1 is a diagram showing the concept of a dew or frost point meter that makes use of the change in the intensity of scattered light and/or reflected light from a reflector mirror.

The operating principle of the method of the present invention is described below with reference to FIG. 1 which shows schematically the concept of an apparatus that is generally called a dew point or a frost point meter.

Shown by $1a$ is a freeze generator and $8a$ is a heater. Shown by $20a$ is a cold head. Compartment A is enclosed with walls $8a$ that are typically made of a good heat conductor such as gold, silver, copper, aluminum, silicon, nickel or chromium. Shown by $5a$ is an inlet for the gas to be measured. Compartment B is enclosed chiefly with walls $7a$ and partly with walls $3a$. A hole $9a$ is made in the interface between the two compartments A and B. Shown by $11a$ is the gap between a reflector mirror $10a$ and the interface between the compartments A and B. At least part of the walls $7a$ of compartment B is formed of a poor heat conductor such as stainless steel, a copper-nickel alloy, glass, ceramics, or plastics (e.g. fluorine resins, polyimide resins and silicone resins). This is in order to prevent compartment A from being cooled by the cold head $20a$. Shown by $6a$ is a gas outlet. Shown by $4a$ is a light source equipped with a condenser lens and may typically be an LED emitting at a given wave-length. Shown by $4a'$ is a photodetector equipped with a condenser lens, and the light emitted from $4a$ and reflected by the reflector mirror $10a$ is condensed as much as possible to be effectively detected by $4a'$. Shown by $2a$ is a photodetector equipped with a condenser lens for detecting the light scattered by the reflector mirror $10a$ when the light emitted from $4a$ is reflected by that reflector mirror $10a$.

Figure 2:
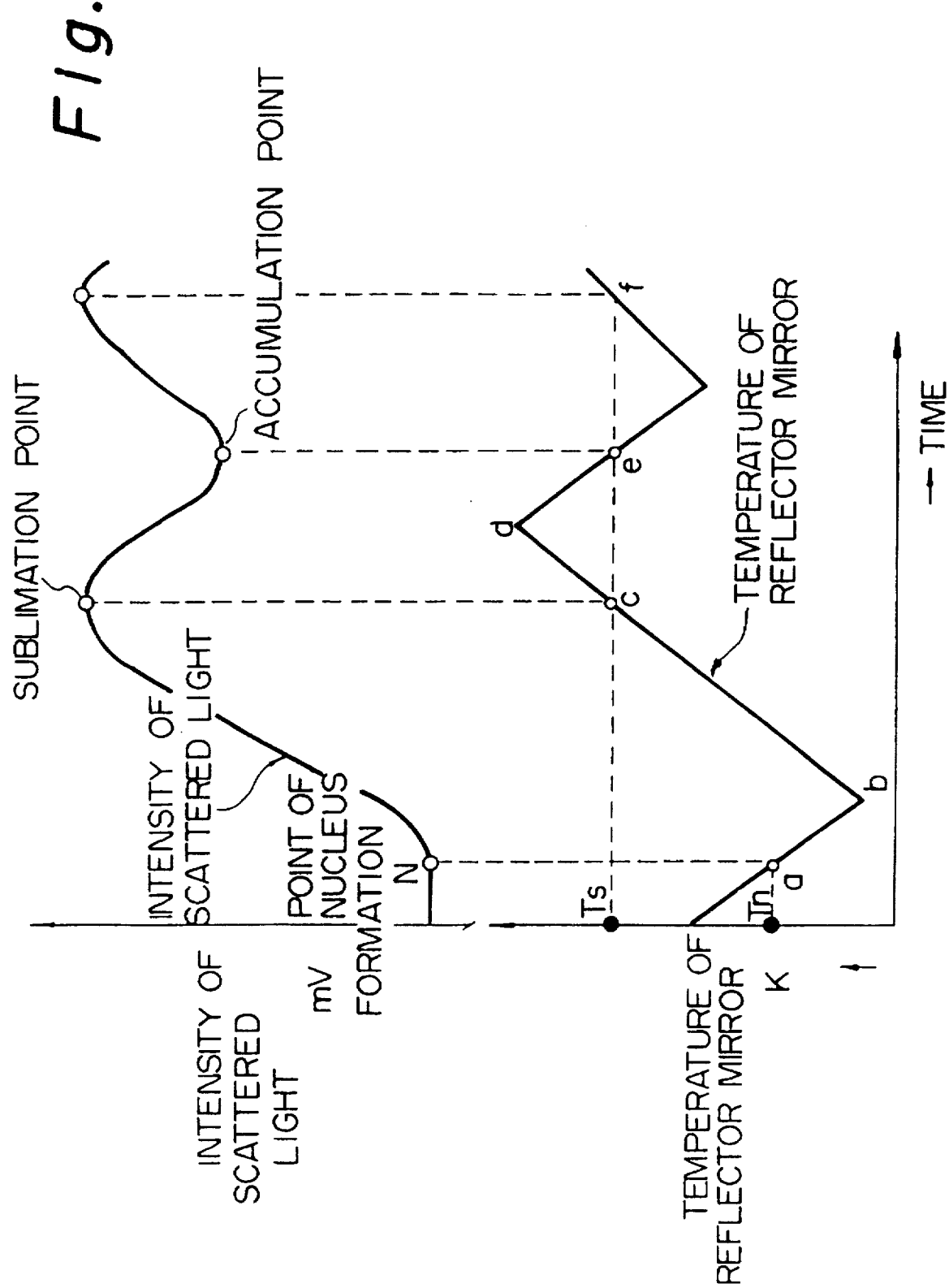
FIG. 2 is a graph showing the relationship between the temperature of the reflector mirror and the intensity of scattered light.
Figure 3:
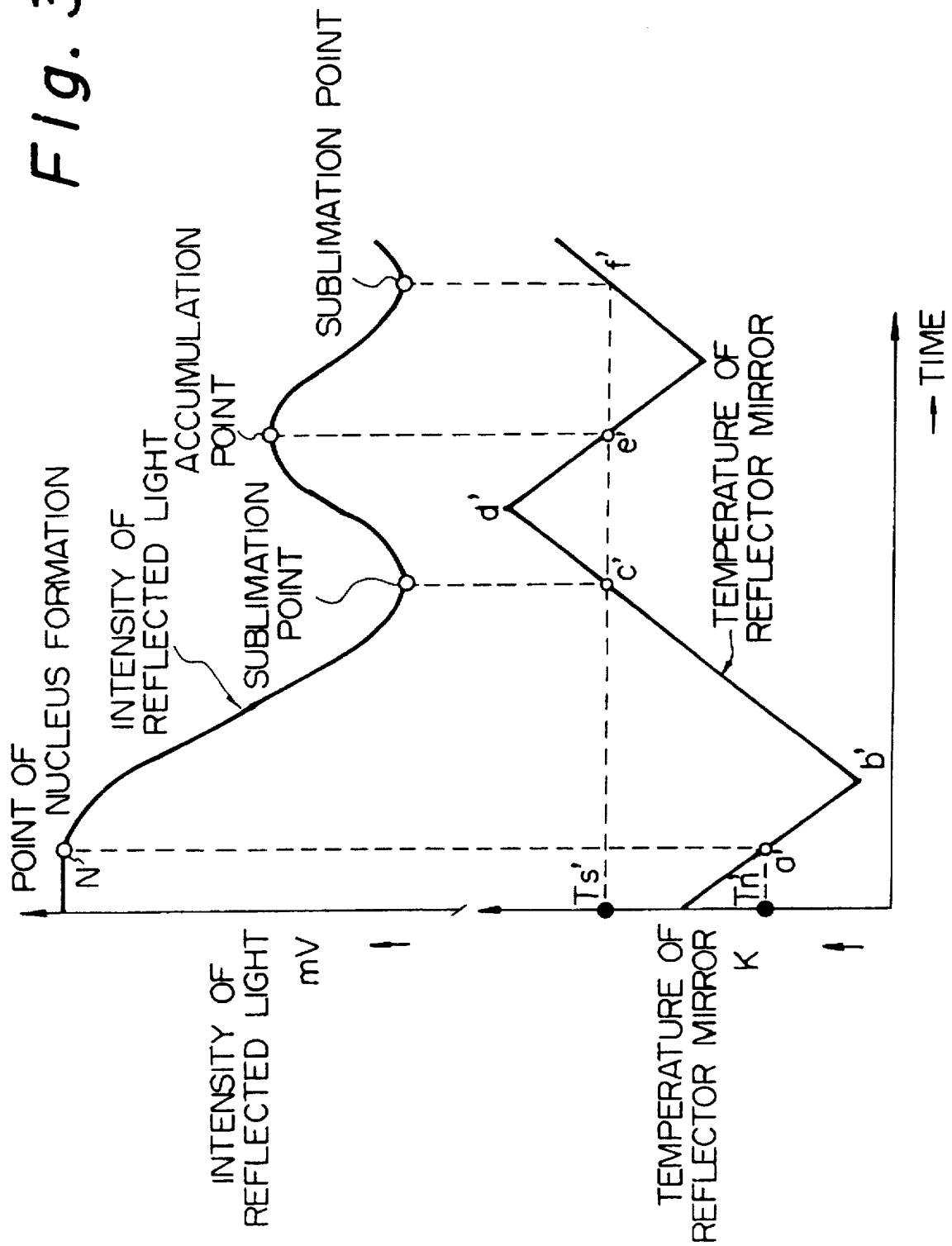
FIG. 3 is a graph showing the relationship between the temperature of the reflector mirror and the intensity of reflected light.

Dew point meters are generally classified as three types, one of the reflected light type which has the light source $4a$ and the reflected light detector $4a'$, another of the scattering type which has the lightsource $4a$ and the scattered light detector $2a$, and the other of the type that detects both reflected and scattered light. Measuring the dew or frost point of a gas of interest using the apparatus described above will proceed in the following manner. First, the gas to be measured is introduced through the inlet $5a$ into compartment A which is controlled at a constant temperature by means of a heater 8' and a thermometer $19a'$. The introduced gas contacts the reflector mirror $10a$ via the hole $9a$, with dew or frost being condensed on that mirror $10a$. The uncondensed gas flows through the gap $11a$ to be discharged from compartment B through outlet $6a$. With the temperature being measured with a temperature sensor $19a$ inserted close to the reflector mirror $10a$, the latter is cooled or heated by a specified method with the freeze generator $1a$ and the heater $8a$. As the reflector mirror is cooled down, dew or frost is condensed on its surface, whereby the light from the light source $4a$ is scattered to increase the intensity of the light received by the photodetector $2a$ equipped with a condenser lens. The profile of the increase in the intensity of light scattering is shown in FIG. 2. Point N is where it can be assumed that the scattered light started to increase and the temperature of the reflector mirror at that point is indicated by Tn corresponding to point a. Similarly, the dew or frost condensed on the surface of the reflector mirror caused the light from the light source $4a$ to be scattered while decreasing the intensity of light being received by the photodetector $4a'$ equipped with a condenser lens. The profile of the decrease in the intensity of light reflection is shown in FIG. 3; point N' is where it can be assumed that the reflected light started to decrease and the temperature of the reflector mirror at that point is indicated by Tn' corresponding to point a'.

The operating principle behind this phenomenon is described below with reference to FIG. 2. When the temperature of the reflector mirror is lowered, dew or frost condensation occurs at point a. However, with the gas being supercooled, point a does not correspond to the correct dew or frost point. In order to make sure that dew or frost condensation has occurred, the temperature of the reflector mirror is further lowered down to point b and subsequently elevated. Needless to say, the gas in this state is supercooled and the ice will continue to grow. Point c where the intensity of scattered light is at a maximum may be designated the subliming point. The temperature of the reflector mirror at that point corresponds to Ts. The profile for the intensity of actual scattered light does not draw a simple parabolic curve it contains but many small ups and dows due to noise as are observed in a record of seismic waves. Hence, the computer will recognize a maximum point of scattered light only some time after the actual maximum point has been reached. In other words, the reflector mirror will be heated even after the actual maximum point (point c) for scattered light has been passed. It is at point d that the computer recognizes that the maximum point for scattered light has been reached and from point d onward, the reflector mirror is cooled again and the intensity of scattered light takes on a minimum value at point e, with the corresponding temperature of The reflector mirror being also Ts. As in the case of the maximum intensity, the background noise causes the computer to recognize the minimum point of scattered light only some time after the actual minimum point has been reached. In other words, the reflector mirror will be cooled even after the actual minimum point (point e) for scattered light has been passed. It is at point f that the computer recognizes that the minimum point for scattered light has been reached and from point f onward, the reflector mirror is heated again.

Thus, it has been verified that the subliming point where the amount of light reception takes on a maximum value and the next occurring of accumulation point of agree to each other with respect to a gas of the same water content; hence, one may safely conclude that Ts corresponds to the correct dew or frost point of the gas of interest. If the cycle of heating or cooling the reflector mirror is repeated, the curve for the scattered light will also change drawing a parabolic pattern. The subliming point and the accumulation point will occur cyclically.

The same principle is further described below with reference to FIG. 3. When the temperature of the reflector mirror is lowered, dew or frost condensation occurs at point a'. However, with the gas being supercooled, point a' does not correspond to the correct dew or frost point. In order to make sure that dew or frost condensation has occurred, the temperature of the reflector mirror is further lowered down to point b' and subsequently elevated. Needless to say,the gas in this state is supercooled and the ice will continue to grow. Point c' where the intensity of reflected light is at a minimum may be designated the subliming point. The temperature of the reflector mirror at that point corresponds to Ts'. Then, the reflector mirror is heated up to point d' which can be regarded as the subliming point, whereupon the ice starts to vaporize and the temperature of the reflector mirror starts to decrease at point d' downward and the intensity of reflected light will attain a maximum level at point e'. The temperature of the reflector mirror at that point also corresponds to Ts'. Thus, it has been verified that the subliming point where the amount of light reception takes on a minimum value and the next occurring point of accumulation agree to each other for a gas of the same water content; hence, one may safely conclude that Ts' corresponds to the correct dew or frost point of the gas of interest. If the cycle of heating or cooling the reflector mirror is repeated, the curve for the reflected light will also change drawing a parabolic pattern. As in the case of detecting scattered light, the subliming point and the accumulation point occur cyclically in the case of detecting reflected light.

Profiles for the cooling and heating rates in the case under consideration are given below.

TABLE 1

| Cooling Rate | | |
|---|---|---|
| Temperature range (°C. → °C.) | | Cooling rate (°C./min) |
| 20 | −70 | 10.0 |
| −70 | −90 | 4.0 |
| −90 | −100 | 2.0 |
| −100 | −105 | 1.0 |
| −105 | −110 | 0.50 |
| −110 | −115 | 0.25 |
| −115 | −120 | 0.13 |
| −120 | −125 | 0.063 |
| −125 | −130 | 0.031 |
| −130 | −135 | 0.016 |

TABLE 2

| Heating Rate | | |
|---|---|---|
| Temperature range (°C. → °C.) | | Heating rate (°C./min) |
| −135 | −130 | 0.016 |
| −130 | −125 | 0.031 |
| −125 | −120 | 0.063 |
| −120 | −115 | 0.13 |
| −115 | −110 | 0.25 |
| −110 | −105 | 0.50 |
| −105 | −100 | 1.0 |
| −100 | −90 | 2.0 |
| −90 | −70 | 4.0 |
| −70 | 30 | 10.0 |

Equation (1) is a formula for a curve. The lower the temperature, the slower the heating and cooling rates. In the case under consideration, the rate of cooling from 20° C. to −70° C. is 10.0° C./min whereas the rate of cooling from −130° C. to −135° C. is 0.016° C./min. If it is assumed that cooling or heating is conducted following the curved path represented by Equation (1), the heating or cooling rate must be slowed down at decreasing temperature and to achieve this, performing a fully computer-aided control is ideal. However, this approach is not economical.

The common practice is to lower the cooling or heating rate stepwise as shown in Tables 1 and 2 above. For example, at temperatures below −100° C., the cooling or heating rate is varied for every decrement of 5° C.

Varying the heating or cooling rate stepwise following the curved path represented by Equation (1) means substantially the same as illustrated by Tables 1 and 2.

Figure 4:
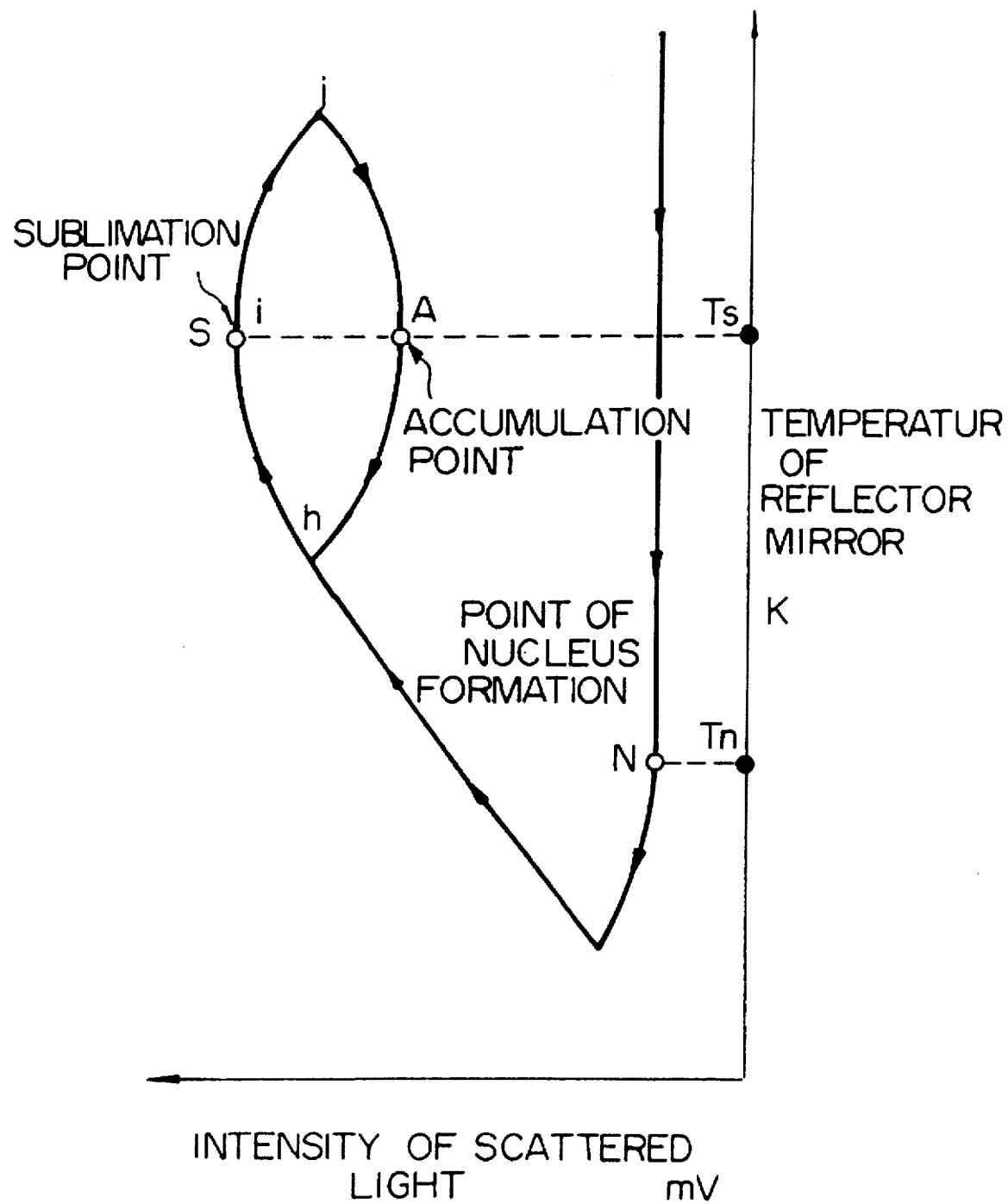
FIG. 4 is a graph showing, in association with FIG. 2, the relationship between the intensity of scattered light, the point of nucleus formation, the subliming point and the accumulation point of solidification of the topmost layer.

FIG. 4 is a graph showing the relationship between the temperature of the reflector mirror and the intensity of scattered light with respect to a similar method of measurement. Since the reflected light is the same as the scattered light except that the variation in intensity is reversed, the following description concerns only the scattered light and no description is made about the reflected light.

When the cycles of heating and cooling the reflector mirror are repeated, the intensity of scattered light changes drawing a parabolic curve to form a loop as shown in FIG. 4.

Figure 5:
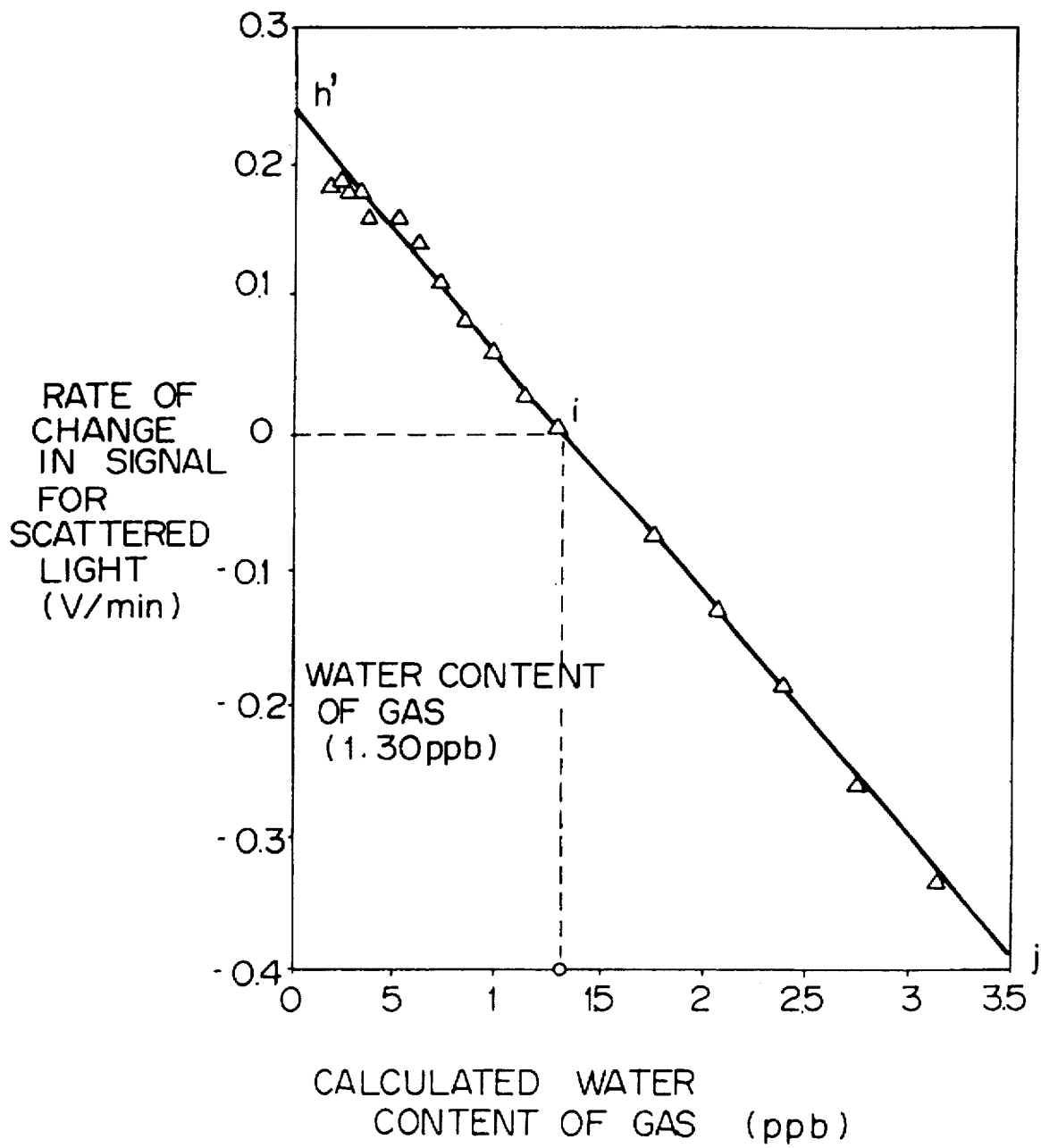
FIG. 5 is a graph used (in the present invention) for determining a maximum point on a straight line constructed by differentiating the curve shown in FIG. 2 or 4.

FIG. 5 is a graph showing the relationship between the water content of a particular gas and the rate of change in a signal for scattered light. Referring back to FIG. 4, the intensity of scattered light changes at points h, i and j drawing a curve when the temperature of the reflector mirror is varied. Assuming that the curve connecting points h, i and j represents a quadratic function, one may differentiate it and plot the result on a straight line, as shown in FIG. 5. In FIG. 5, points h', i' and j' correspond respectively to points h, i and j in FIG. 4. The water content of the gas as plotted on the horizontal axis represents the value as determined from the equation for the vapor pressure of ice.

One may safely conclude that the gas under consideration had a water content of 1.30 ppb. The conditions of the experiment were as follows:

$T_0 = -90°$ C.
$R(T) =$ ca. 4° C./min
$n =$ ca. 0.67
$\Delta T =$ ca. 0.4° C.

Sample measured once for every two seconds.

Another characterizing part of the present invention is that it makes a special provision for the error resulting from noise that will unavoidably occur in measurements of the type contemplated by the present invention. If the peak intensity of scattered light is taken as the point of dew or frost condensation, noise makes it very difficult to read the correct point. However, if the point of dew or frost condensation is to be derived from the crest of a peak or the bottom of a valley as in the present invention, one may plot the actual points on the straight line obtained by differentiating a quadratic curve and determine the point of dew or frost condensation at the crest of a peak on the straight line obtained by the method of least squares. This insures the operator to obtain very precise and stable values even in the presence of noise.

Figure 6A:
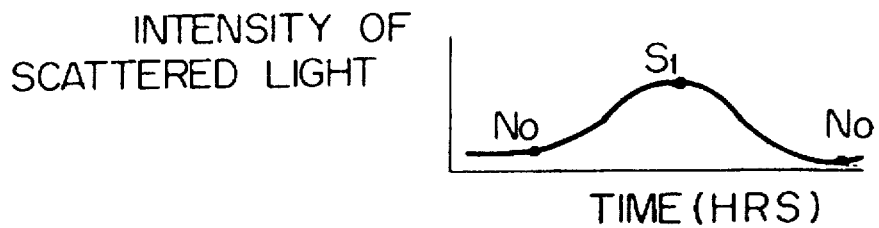
FIGS. 6A and 6B are graphs showing the cycle times of the point of nucleus formation and the subliming point as measured at low dew points (in the prior art)
Figure 6B:
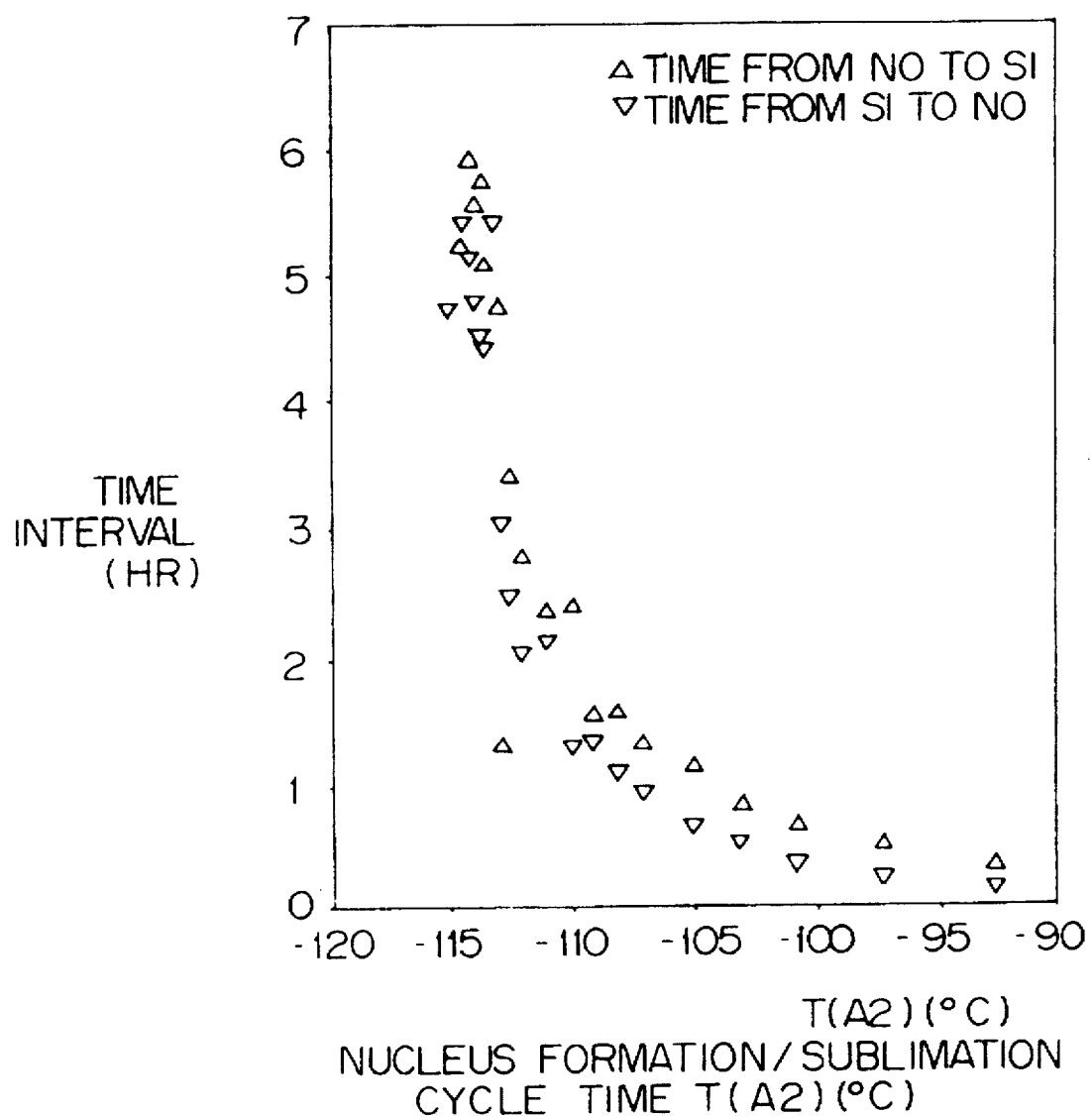

FIGS. 6A and 6B show the time from the point of dew or frost formation (No) to the point ($S_1$) where the intensity of scattered light reached a maximum, as well as the time from point $S_1$ to the point where the dew or frost disappeared in the prior art method. Obviously, the prior art method took quite a long time to complete measurements.

FIGS. 7A and 7B show the relationship between the accumulation point (A) and each of the two subliming points ($S_1$ and $S_2$) as detected by the method of the present ivnention. Obviously, the time of measurement was drastically shortened when the method of the present invention was adopted.

Applications of low-temperature optical dew point meter

Described below are several examples of measurement with a low-temperature optical dew point meter.

Tube cleanup

Figure 8:
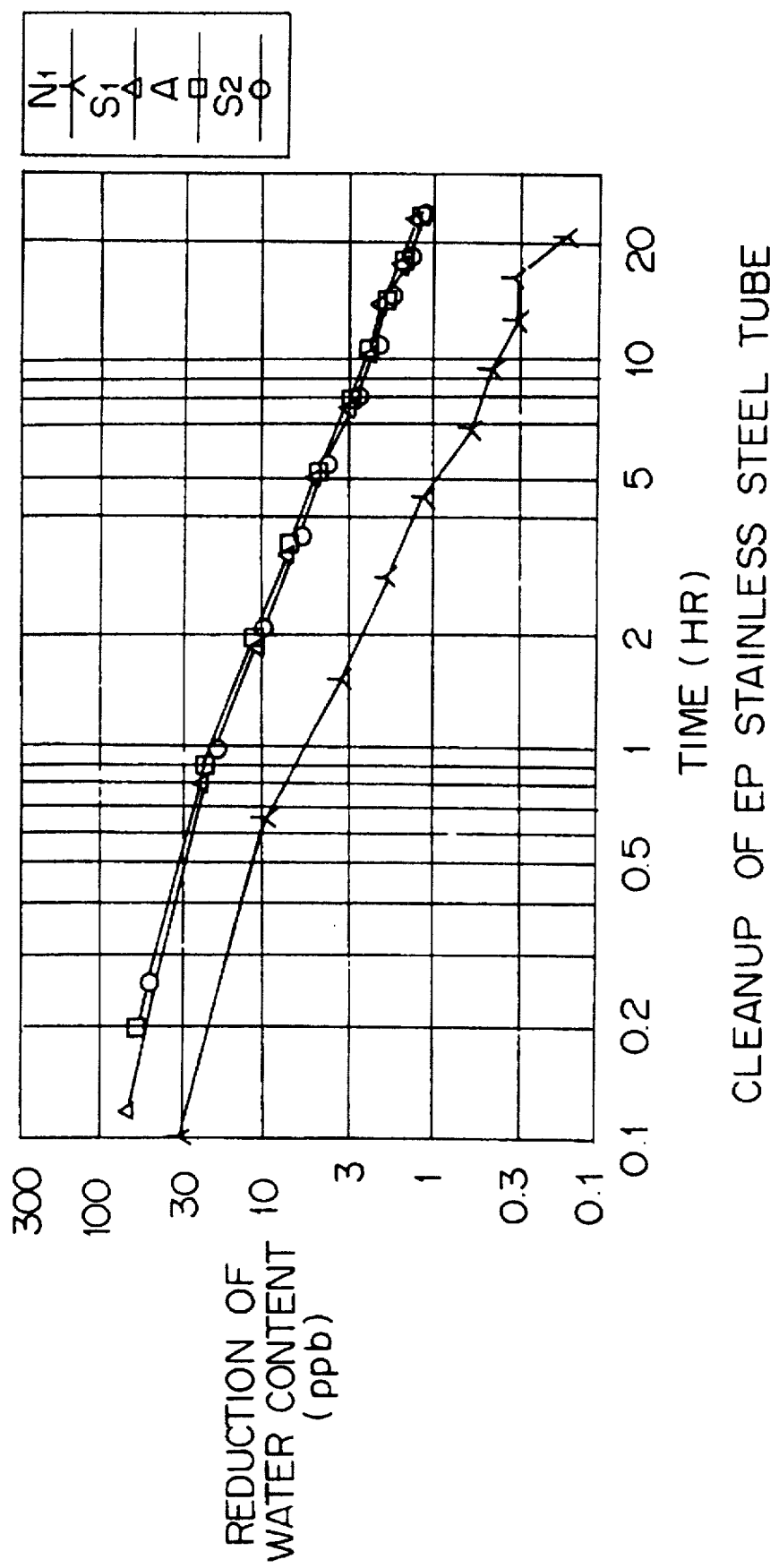
FIG. 8 is a graph showing the profile of tube cleanup.

An EP tube of stainless steel (SUS 316L) that had a diameter of ¼ inch and the inner surface of which was electropolished was left to stand in atmospheric air as $N_2$ gas purified with a zirconium getter purifier (SAES Getters S.p.A.) was allowed to flow through the tube and the phenomenon of tube cleanup was examined. The time profiles of the point of dew condensation (No) as measured by the prior art method, as well as the temperatures at the three points ($S_1$ A, $S_2$) for determining the points of equilibria are shown in FIG. 8. For convenience sake, the plots of both the points of equilibria and the point of dew condensation were computed from the equation for a curve of the vapor pressure of ice. According to FIG. 8, the points of equilibria decreased almost linearly irrespective of the differences in S, A and S, giving a good approximation for the phenomenon of water desorption from the inner surface of the tube. On the other hand, the point of dew condensation was lower and less stable than the points of equilibria.

Effectiveness of passivation treatment with $O_2$

Figure 9:
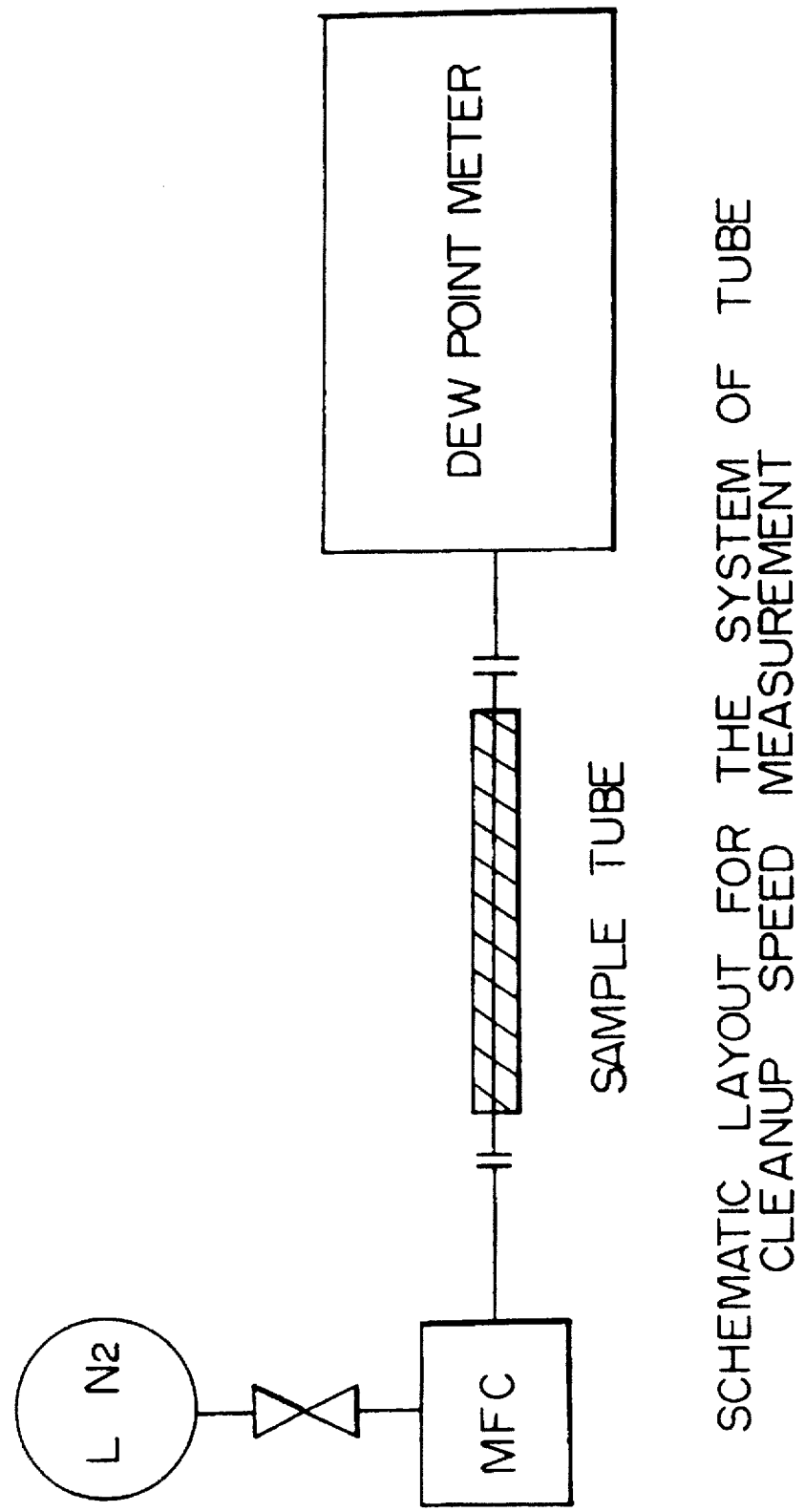
FIG. 9 shows a system for measuring the tube cleanup speed.

The above-mentioned electropolished (EP) tube of stainless steel (SUS 318L) was compared with an $O_2$ passivation treated tube that was the same as the EP tube except that it was heat treated with an oxygen gas of low dew point. The measurement system used is shown in FIG. 9. The purifying gas was a nitrogen gas of very low dew point that was prepared by vaporizing liquid nitrogen. With its flow rate being controlled with a MFC (mass flow controller), the $N_2$ was permitted to flow through the tube of interest and the cleanup speed was measured. Two tube sizes were selected: ⅜ inch and 1 inch o.d.

Figure 10:
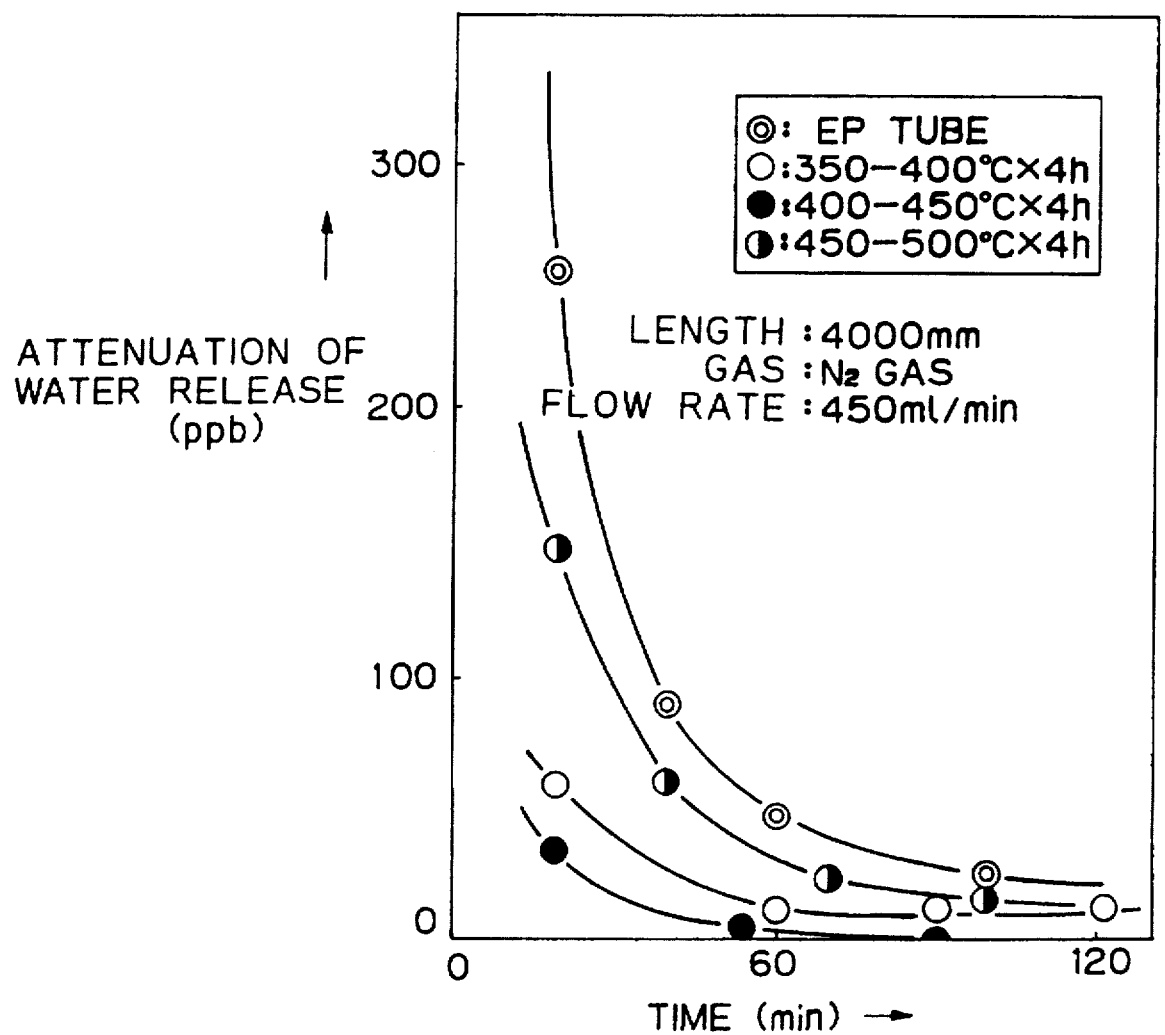
FIG. 10 is a graph showing the profile of a tube cleanup experiment.
Figure 11:
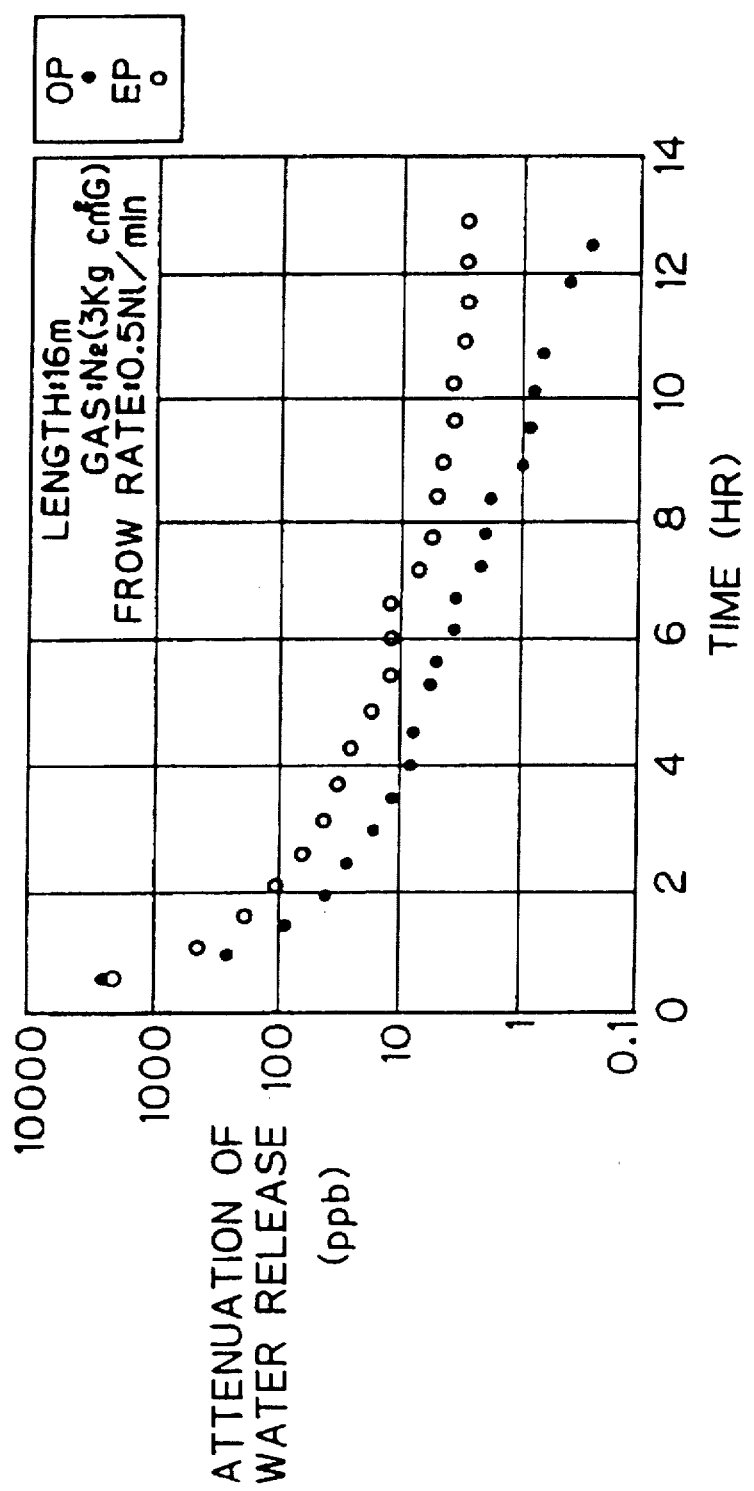
FIG. 11 is a graph showing the profile of another tube cleanup experiment.

As for the tubes with the o.d. ⅜ inch, measurements were also conducted for varying temperatures of the passivation treatment with $O_2$. The results are shown in FIG. 10, from which one can see that the cleanup speed was the lowest with the unpassivated EP tube whereas it was the highest with the tubes passivated at 400° C.–450° C. One can also see from FIG. 10 that the behavior of water release from the inner surface of tube varied with the temperature for treatment and that, inversely, an optimum temperature for treatment can be determined from the behaviour of water release. FIG. 11 shows the results of cleanup on a SUS 316L EP tube (1 inch$^\phi$) and a 16-m long EP tube that was subjected to passivation with $O_2$ of low dew point.

Relationship between dew point and water content

As is well known, the dew point can be converted to the water content and vice versa and, as a matter of fact, the water content is currently expressed in terms of such units as ° C. and ppm. Various methods of conversion are described below. A water content meter has such an operating principle that it measures the water content and converts it to a dew point. On the other hand, a dew point meter measures the dew point and converts it to a water content. To convert from one parameter to the other, the saturated vapor pressure of water is used and a calculation is made in terms of the ratio of partial pressure to total pressure. Since the saturated vapor pressure is a function of temperature, the ratio of partial pressure to total pressure at a given temperature will provide a simple means of determining the relationship between dew point and water content. Generally speaking, the dew point is determined from the point of phase transition at one atmosphere, namely, the point of dew (frost) condensation, and the total pressure is assumed to be one atmosphere. The method, however, has several problems, as described below. (1) A number of experimental formulas have been reported to describe the curve for the saturated vapor pressure of water but they differ from one another by small degrees; and (2) Since the saturated vapor pressure is used as a key parameter, conversion is possible only in the case where a complete equilibrium, or a saturated state, is to be measured.

Only after these points are taken into account, it is possible to perform a conversion from dew point to water content and vice versa. JIS K 0512 ("Hydrogen" ) lists a table of conversion between dew point and water content down to −100° C. but it is of no help at temperatures below −100° C. The only alternative for conversion is to use a line of extrapolation from the curve for the saturated vapor pressure of water as constructed in the manner described above. The formula that is known to be the most reliable today is:

$$\log_{10} \text{oP}_{H_2O} = -2445.5646/T + 8.2312 \log^{10}T - 0.01677006T + 1.20514 \times 10^{-5}T^2 - 6.757169$$

$C = P_{H_2O}/760.10^9$ where

T: dew point on the absolute scale (K)
$P_{H_2O}$: the saturated vapor pressure of water (mmHg)

C: water content (ppb)

This formula is given in International Critical Tables of Numerical Data, Physics, Chemistry and Tehcnology, Volume III, p.210, National Research Council of USA (1928).

Figure 12:
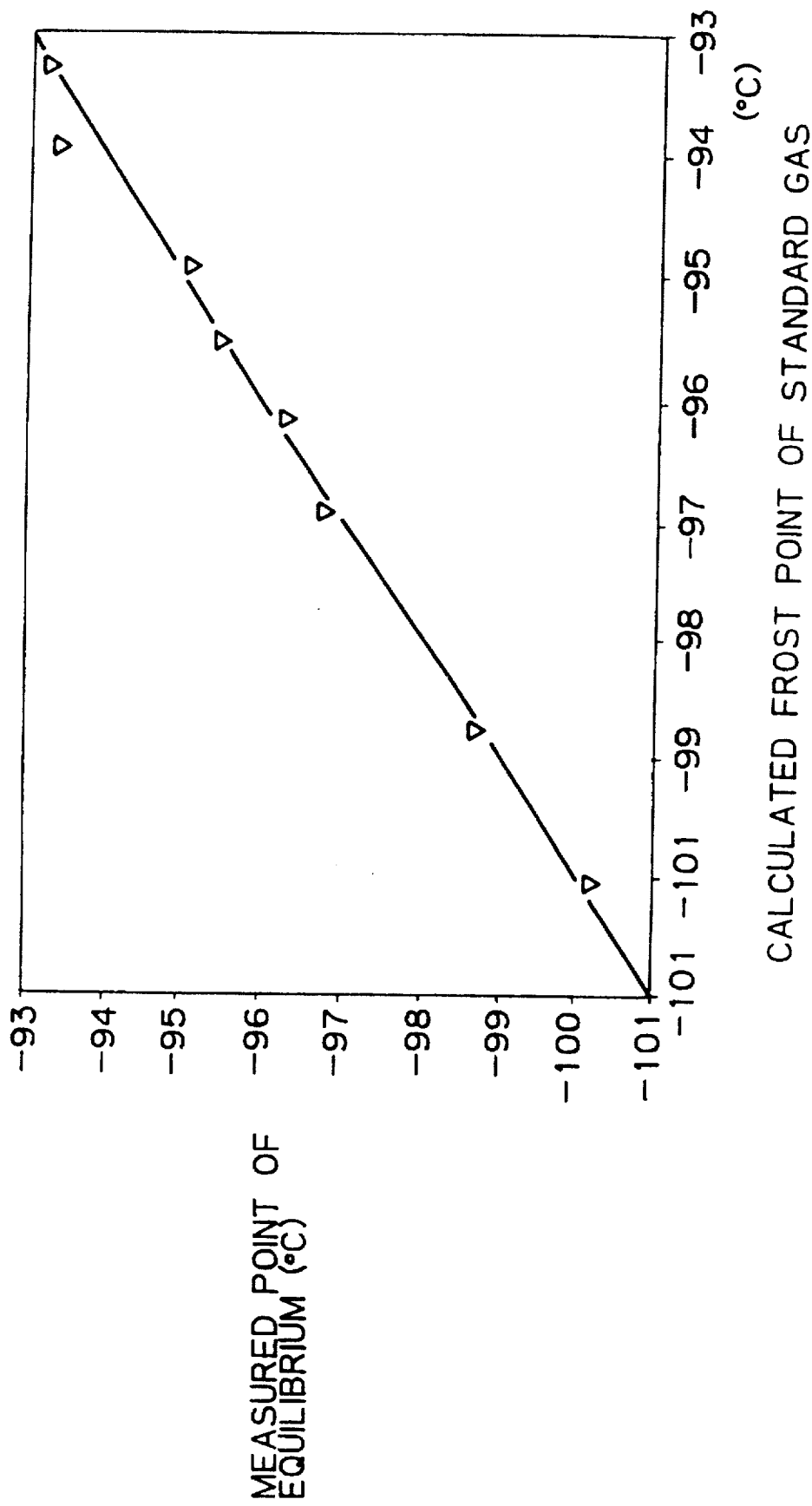
FIG. 12 is a graph showing the relationship between the frost point of a standard gas and a measured point of equilibrium.
Figure 13:
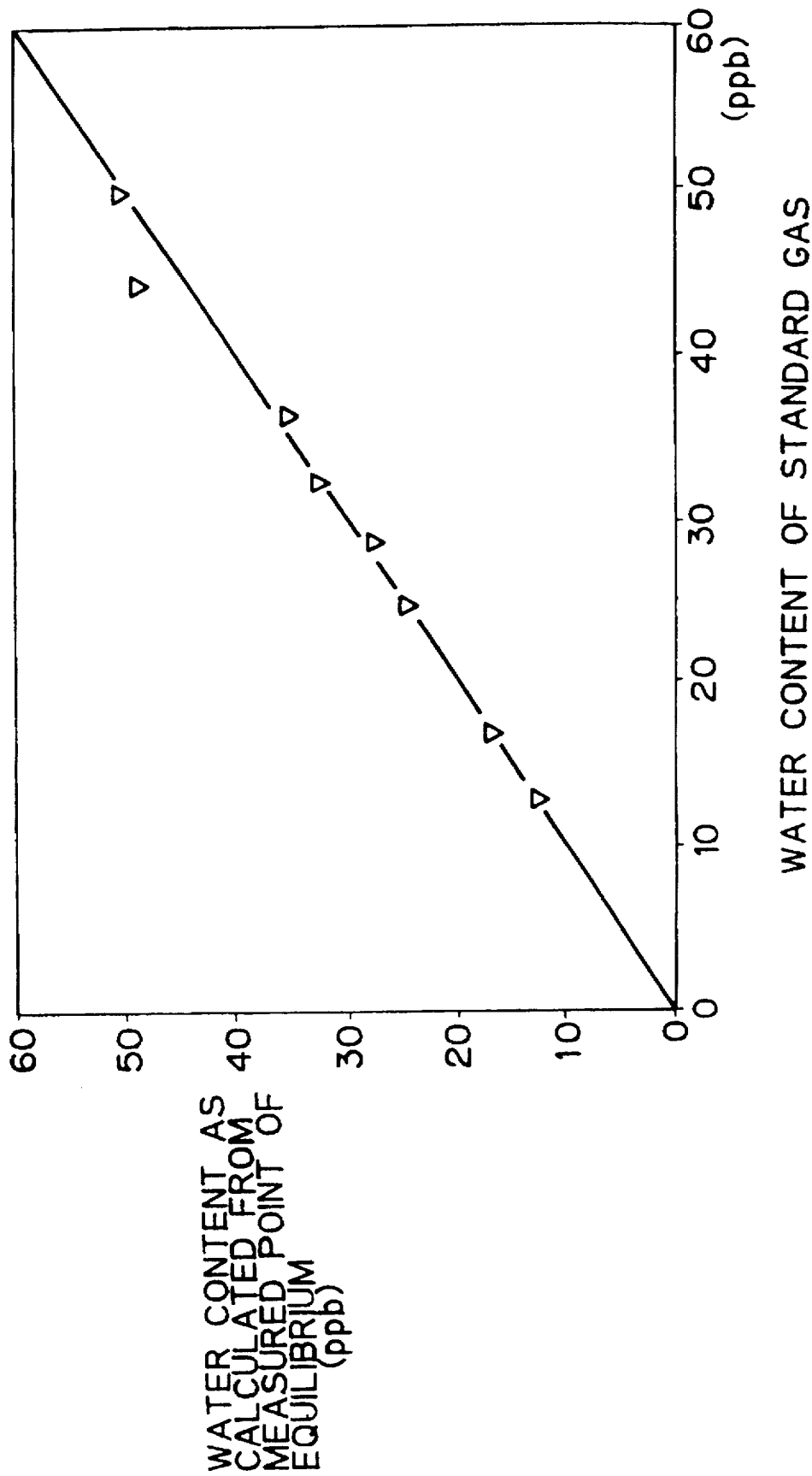
FIG. 13 is a graph showing the water content of a standard gas and a measured water content as calculated from measured point equilibrium.

FIG. 12 shows the relationship between the frost point of a standard gas (with a known water content) as calculated from the water content and the point of equilibrium (° C.) as measured in accordance with the present invention. FIG. 13 shows the relationship between the water content of a standard gas and the water content as calculated from the actually measured point of equilibrium. It is obvious from FIGS. 12 and 13 that the method of the present invention enables the water content of a gas to be measured in a very precise way. The apparatus used in the experiment for generating the standard gas was a model from Hitachi Tokyo Electronics Co., Ltd. (see FIG. 14), in which 30 ppm of a standard gas was diluted through two stages to generate the desired standard gas.

This invention also relates to an apparatus for carrying out the method of the invention, said apparatus comprising:

(i) compartment A made of a good heat conductor;

(ii) an inlet for the gas to be measured, which inlet is provided on compartment A;

(iii) a heater for adjusting the temperature in compartment A, and a temperature sensor;

(iv) compartment B provided adjacent to compartment A, at least part of compartment B being made of a poor heat conductor;

(v) a hole or nozzle provided at the interface between compartments A and B;

(vi) a reflector mirror having a temperature sensor, said reflector mirror being provided on compartment B in such a way as to cover the hole or nozzle, and said mirror being connected thermally to a freeze source in such a way that it can be freely varied in temperature from room temperature to −80° C. or below;

(vii) a gas outlet provided on compartment B;

(viii) a small gap formed between said hole or nozzle and said reflector mirror;

(ix) a device that allows convergent rays of light or laser light to be emitted onto the surface of the reflector mirror;

(x) a light-receiving device that projects condensed rays of light or laser light onto the frost formed on the surface of the reflector mirror, thereby detecting the change in the intensity of scattered light and/or reflected light; and (xi) a detector device that senses the temperature at which the condensation of dew or frost occurred on the reflector mirror.

This invention also relates to an apparatus for carrying out the method of the invention, said apparatus comprises:

(i) a reflector mirror whose temperature can be changed from room temperature to a point less than −80° C.;

(ii) a gas inlet or a gas blowing nozzle for supplying a sample gas into a compartment including said reflector mirror in such a way that said sample gas will contact said reflector mirror;

(iii) a source of condensed light or laser light;

(iv) a device for projecting condensed rays of light to that part of the relector mirror where dew or frost is to form;

(v) a mechanism for detecting the change in the intensity of scattered light due to the dew or frost formed on the reflector mirror; and (vi) a mechanism for detecting the temperature at which the change in the intensity of scattered light was detected, the improvement wherein said scattered light is detected with a light-receiving device provided in two or more directions.

The present invention is described below from a mechanistic viewpoint with reference to accompanying drawings. The dew point meter shown in those drawings is merely intended for illustrative purposes and will in no way limit the scope of the present invention.

FIG. 5 shows an embodiment of the present invention. Shown by 1 is a freeze generator; 2 and 2' are each a heater; 3 is a cold head; 4 is compartment A which is made of a good heat conductor such as gold, silver, copper, aluminum, silicon, nickel or chromium; 5 is a window made of a light-transmissive material such as glass; 6 is an inlet for supplying a sample gas to be measured; 7 is compartment B, with a hole 9 being formed in the wall 8 at the interface between commmpartment A 4 and compartment B 7; 10 is a reflector mirror positioned on top of a heat conductor 20 in such a way as to cover the hole 9. The heat conductor 20 is made of a material that conducts heat as well as the material of which compartment A 4 is made. Shown by 11 is the gap between the reflector mirror 10 and the interfacial wall 8. The gap 11 is preferably as small as possible but if it is designed to be extremely small, the slightest manufacturing error can potentially cause the reflector mirror 10 to contact the interfacial wall 8. To avoid this possibiility, the gap 11 preferably has a size of 0.1–2.0 mm. At least part of compartment B is made of stainless steel, a Cu—Ni alloy, glass, ceramics or plastics (e.g., a fluorine resin, a polyimide resin, a silicone resin). This is in order to insure that compartment A will not be chilled by the cold head 3. If compartment A is chilled excessively, moisture will be adsorbed on the inner surface of that compartment and a low water content may sometimes be read since not all of the moisture content is condensed on the mirror surface. If only one compartment exists, the cell will be cooled in entirety and depending on the selection of material in the cell, it may occur that part of the cell becomes colder than the mirror surface and subsequent moisture condensation in that part will lead to occasional failures to provide highly reproducible results of measurements.

Shown by 12 is a gas outlet: 18 is a condenser lens: 14 is a light source which may be a light-emitting diode: 15 is a condenser lens; 16 is a photodetector: 17 and 18 are each an optical fiber: and 19 and 19' are each a thermocouple or a resistance thermometer and they are inserted to measure the temperatures of the reflector mirror and compartment A.

A measurement of the water content of a gas with the apparatus shown in FIG. 1B will proceed as follows. First, the gas to be measured is supplied through the inlet 6 into compartment A 4 which is controlled at a given temperature by means of heater 2' and temperature sensor 19'; the gas flows through the hole 9 to make contact with the reflector mirror 10, thereby forming dew or frost on it; the uncondensed gas passes through the gap 11 to be discharged from compartment B through the outlet 12; the gap 11 is small enough to insure that-the gas flowing from compartment A to compartment B through the hole 9 will not fail to contact the reflector mirror 10: the light from the light source 14 is converted by the condenser lens 18 in such a way as to form a beam spot that is focused as much as possible on the surface of the reflector mirror 10. The change in the intensity of scattered light due to dew or frost condensation is measured with the combination of the condenser lens 15 and the detector 16, thereby determining the dew point or frost point of the sample gas. The temperature occurring in that case is measured with the temperature sensor 19. The rate of cooling or heating the reflector mirror 10 can be controlled in any desired way by the combination of the heater 2 and the temperature sensor 19.

A helium refrigerator (not shown) may typically be used in the freeze generator but other freezing media such as liquefied nitrogen may also be used.

Figure 15:
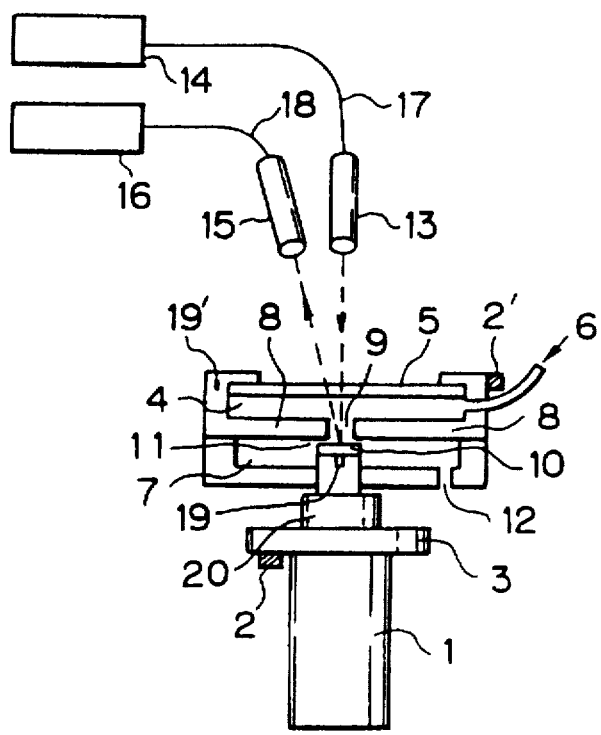
FIG. 15 is a flowsheet for an apparatus according to a preferred embodiment of the present invention.
Figure 16:
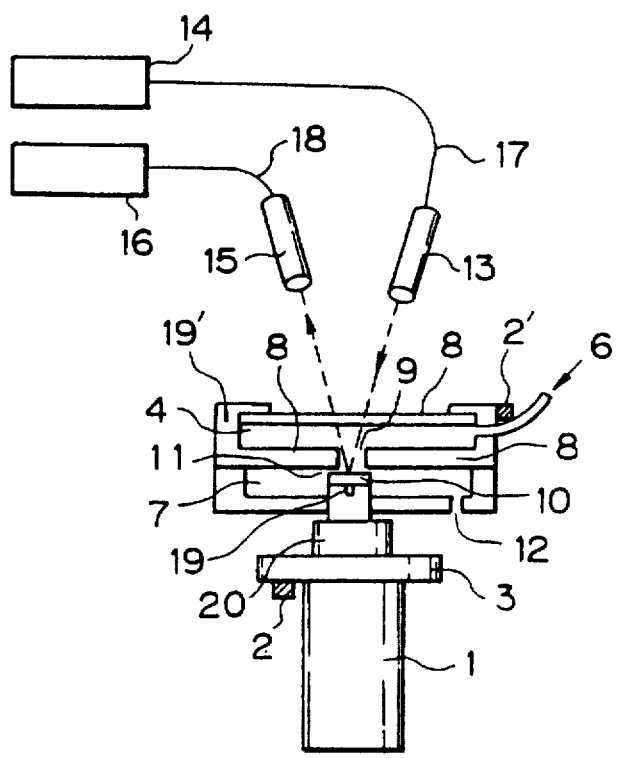
FIG. 16 is a flowsheet for an apparatus according to another preferred embodiment of the present invention.

FIG. 15 illustrates an embodiment in which the change in the intensity of scattered light is measured with the condenser lens 15 and the detector 16. Shown in FIG. 16 is an embodiment in which a lens 13 is positioned in such a way that illuminating light is projected at an angle above the reflector mirror 10 and the condenser lens 15 is positioned on the optical axis of the reflected light. Thus, the present invention is applicable to the measurement of the changes in the intensity of both types of light, scatterd light and reflected light.

Figure 17:
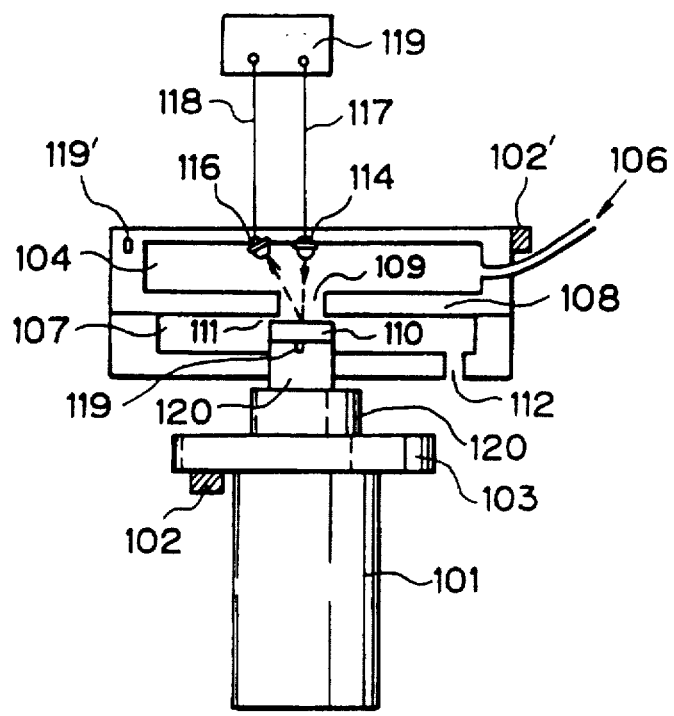
FIG. 17 is a flowsheet for an apparatus according to still another preferred embodiment of the present invention.
Figure 18:
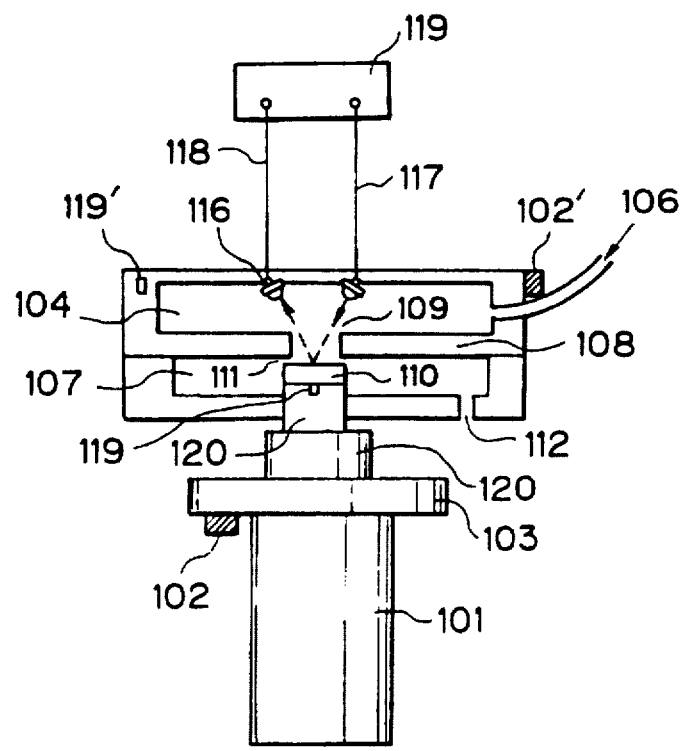
FIG. 18 is a flowsheet for an apparatus according to yet another preferred embodiment of the present invention.

FIG. 17 shows another embodiment of the present invention. Shown by 101 is a freeze generator; 102 and 102' are each a heater; 103 is a cold head; 104 is compartment A which, as in the embodiment shown in FIG. 15, is made of a good heat conductor. Shown by 106 is an inlet for supplying a gas to be measured, and 107 is compartment B, with a hole 109 being formed in the wall 108 at the interface between compartment A 104 and compartment B 107; 110 is a reflector mirror positioned on top of a heat conductor 120 in such a way as to cover the hole 109. Shown by 111 is the gap between the reflector mirror 110 and the interfacial wall 108. For the size of the gap 111 and the constituent material of compartment B, see the remarks given in connection with the embodiment shown in FIG. 15. Shown by 112 is a gas outlet, and 119 and 119' are each a thermocouple or a resistance thermometer and they are adapted to function independently of each other to measure the temperatures of the reflector mirror and compartment A. Thus, as in the embodiment shown in FIG. 15, the primary object of the temperature sensor 119 is to measure the frost point but it can also be used for the purpose of controlling the operation of the helium refrigerator and the heater 102 so that the temperature at the surface of the reflector mirror 110 can be freely varied. The purpose of the temperature sensor 119' is to control the temperature in compartment A at will as the heater 102' is operating. The only differences from the embodiment shown in FIG. 15 are as follows: compartment A has no light-transmitting window; the light source 114 such as a light-emitting diode equipped with a condenser that is provided in compartment A and the detector 116 equipped with a condenser lens for receiving scattered light will project light onto the dew or frost formed on the reflector mirror and receive the resulting scattered light; and electric wires 118 and 117 and an electric circuit 119 for signal transmission and reception are provided outside the cell of the dew point meter. FIG. 18 shows the case where the change in the intensity of light from the light source 114 which has been reflected by the reflector mirror 110 is detected with the detector equipped with a condenser lens.

Figure 19:
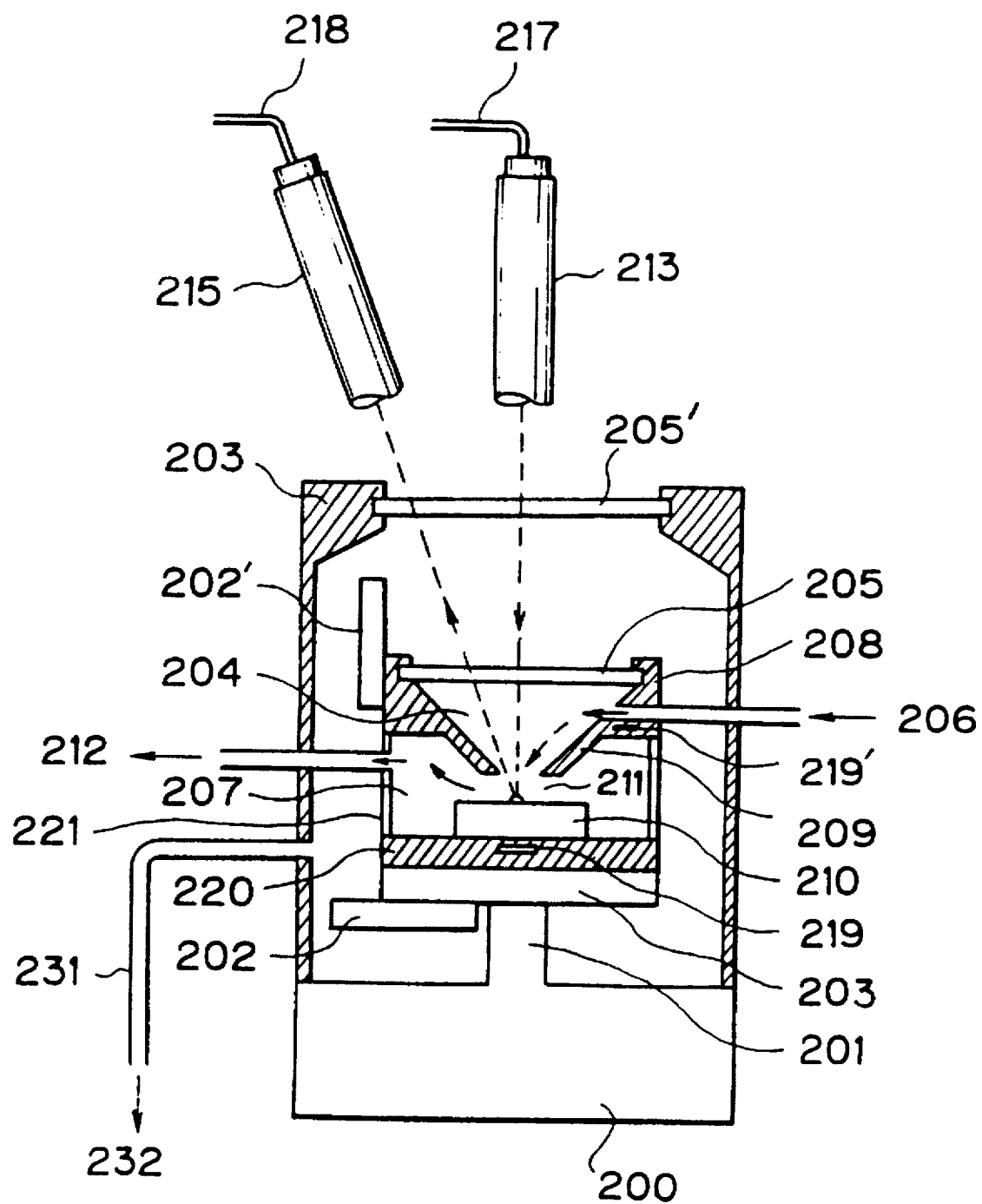
FIG. 19 is a flowsheet for an apparatus according to a still preferred embodiment of the present invention.

FIG. 19 shows still another embodiment of the present invention. Shown by 201 is a freeze generator; 200 is a helium refrigerator; 202 and 202' are each a heater; 203 is a cold head; 204 is compartment A; 206 is an inlet for supplying a gas to be measured; 207 is compartment B. Instead of a hole, a nozzle with a mild slope is provided at the interface between compartment A 204 and compartment B 207. A reflector mirror 201 is provided on top of a heat conductor 220 in such a way as to cover the nozzle 209. Shown by 211 is the gap between nozzle 209 and reflector mirror 210. As in the case shown in FIG. 15, the wall 208 of compartment A is made of a good heat conductor and the wall of compartment B in part 221 is made of a poor heat conductor. Shown by 212 is a gas outlet; 219 and 219' are each a thermocouple or a resistance thermometer; 202 and 202' are each a heater; 230 is a casing. The air in the casing 230 is discharged through a pipe 231 by means of a vacuum pump (not shown) in order to create a vacuum and thermally insulated condition. Shown by 205 and 205' are each a glass window capable of highly efficient light transmission. Light issuing from a light source such as a light-emitting diode is guided through an optcal fiber 217, condensed by a condenser lens 213, projected onto a reflector mirror 211 and scattered by its surface. The scattered light passes through a condenser lens 215 and is guided thorugh an optical fiber 218 to be transmitted to a photodetector (not shown).

Figure 20:
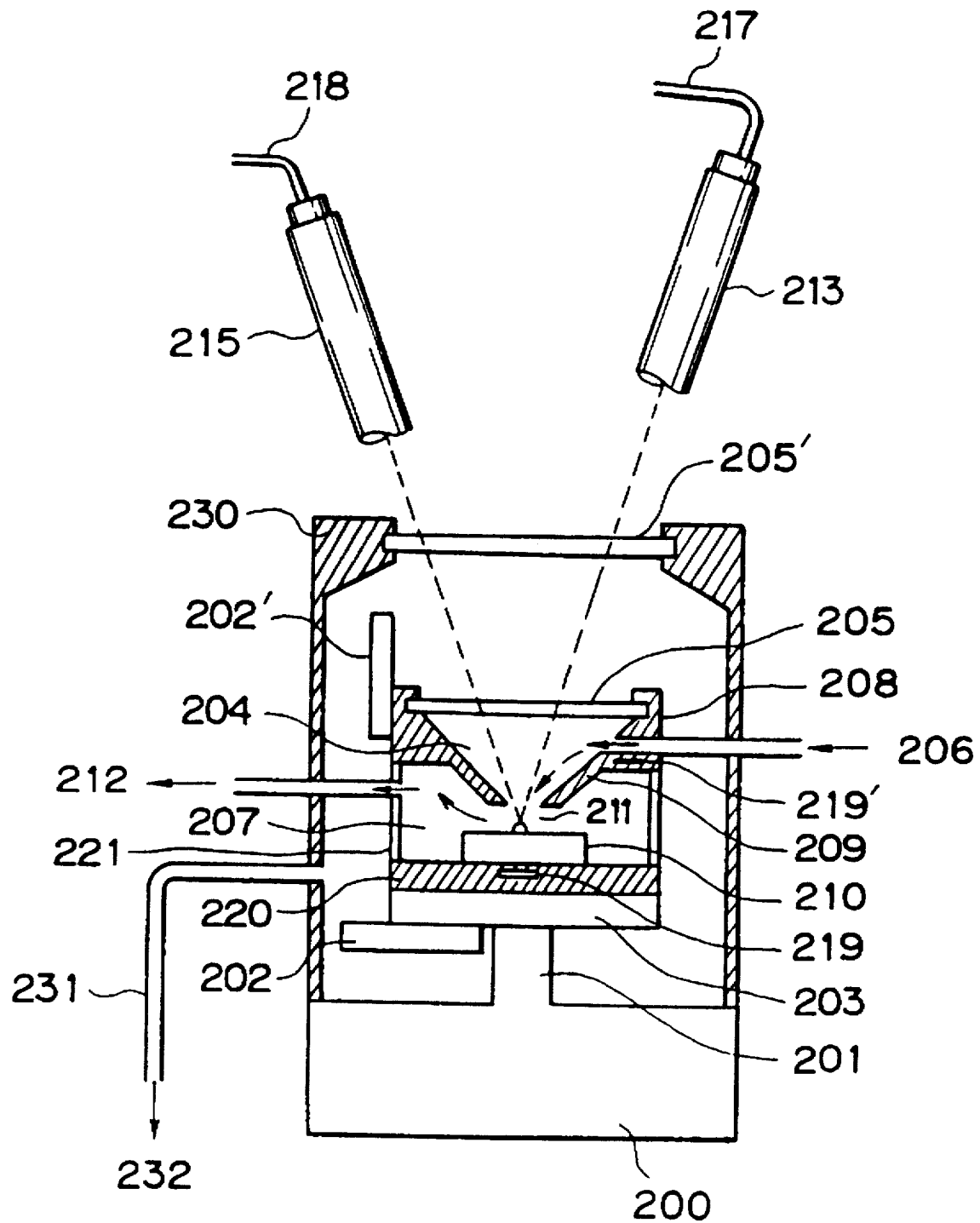
FIG. 20 is a flowsheet for an apparatus according to another preferred embodiment of the present invention.

The only difference from the first embodiment shown in FIGS. 15 and 16 is that a nozzle is provided between compartments A and B. The other features and their operations are completely the same and will not be described in detail. FIG. 20 shows an embodiment in which the light condensed by a condenser lens 213, projected onto a reflector mirror 211 and reflected from its surface passes through a condenser lens 215 provided on the optical axis of the reflected light and is subsequently guided through an optical fiber 218, whereupon the change in the intensity of received light is detected.

In the apparatus described above, compartment A preferably has an inner capacity of 0.5–5 ml. Compartment A may have any shape as seen in plan view.

In the figures mentioned above, compartment A is shown to be positioned above compartment B. Inversely, compartment B may be positioned above compartment A. If desired, both compartments A and B may be juxtaposed on a horizontal plane.

Figure 21:
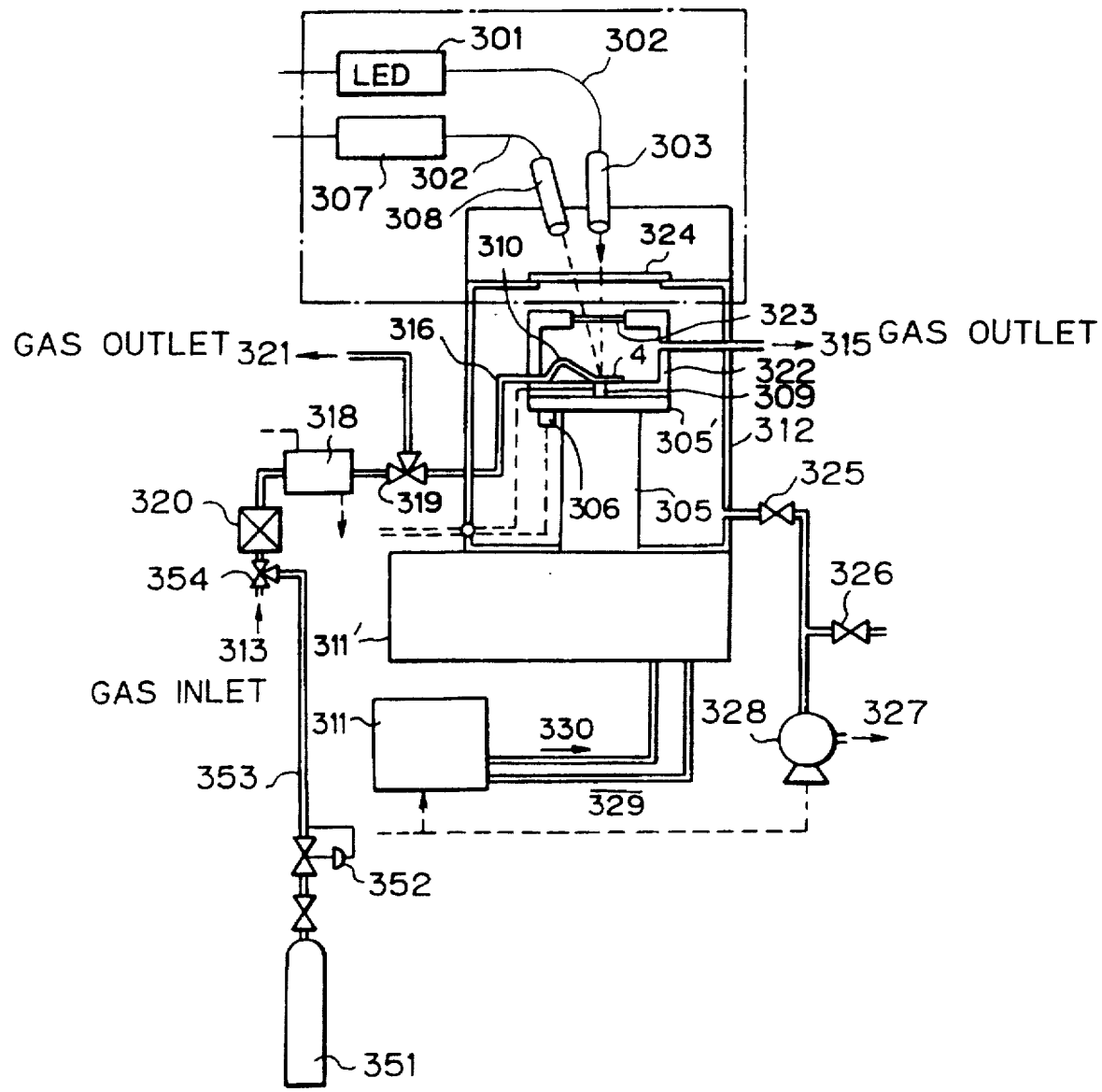
FIG. 21 is an apparatus preferred for implementing the present invention.

FIG. 21 illustrates the first embodiment of the present invention. A helium refrigerator is used in the cooling system and a helium gas as compressed with a circulating helium compressor 311 is circulated through a loop consisting of a line 330, a drive mechanism 311', a freeze generator 305, the drive mechanism 311' and a line 329. The freeze generator 305 comprises a piston or displacer inserted into a stainless steel cylinder and by driving the piston or displacer vertically by means of the drive mechanism 311', freeze is generated on the cold head 305' at the upper end of the cylinder 305. A metallic cell (hereunder referred to simply as the "cell") 322 is disposed in such a way as to insure adequate thermal contact with the cold head 305. The cell 322 is partly formed of a light-transmissive material 323 such as glass. A reflector mirror 304 in the form of a smooth-surfaced silicon wafer is placed on the bottom of the cell 322 in such a way as to insure adequate thermal contact. A temperature sensor 309 such as a thermocouple or a resistance thermometer is inserted into the bottom wall of the cell 322.

A sample gas to be measured for dew point is fed into the apparatus through a gas inlet 313, passes through a filter 320, has its flow rate adjusted to be constant by means of an automatic flow adjusting device 318 such as a mass flow controller, and is controlled in flow direction by a three-way valve 319 to be discharged from the system through a gas outlet 321. The sample gas line will reach an equilibrium faster when the volume of gas purge is high than when it is low. The sample gas then flows into the cell 322 via a line 316. The part of the line that penetrates the cell wall and the subsequent portion is made of a thin-walled stainless steel tube and, in the cell 322, the gas is blown against the reflector mirror 304 on the bottom of the cell, from which the gas is discharged through a gas outlet 315. To increase the response speed, the gas line starting from inlet 310 and extending up to part 310 is desirably composed of a tube of a suitable material such as stainless steel that has a diameter of ¼", ⅛", ¹⁄₁₆", etc., that has been electropolished or otherwise treated to provide a smooth inner surface, and that is subjected to less adsorption or desorption of water and water release from the interior.

The light from a light-emitting diode (LED) 301 is guided through an optical fiber 302 to become partly convergent and is further focused to form a beam spot that passes through windows 324 and 323 made of a light-transmisive material to be incident normally on the surface of the reflector mirror 304. To determine the point of frost condensation on the surface of the reflector mirror, the light scattered from it is collected by a condenser lens 8 positioned in a direction exterior to the angle of reflection of the light projected from the lens 303, and the collected light is guided through an opticall fiber 302' and detected with a PN photodiode 307; the point of frost condensation is finally evaluated on the basis of the relationship between the intensity of scattered light and the temperature of the reflected mirror.

Figure 14:
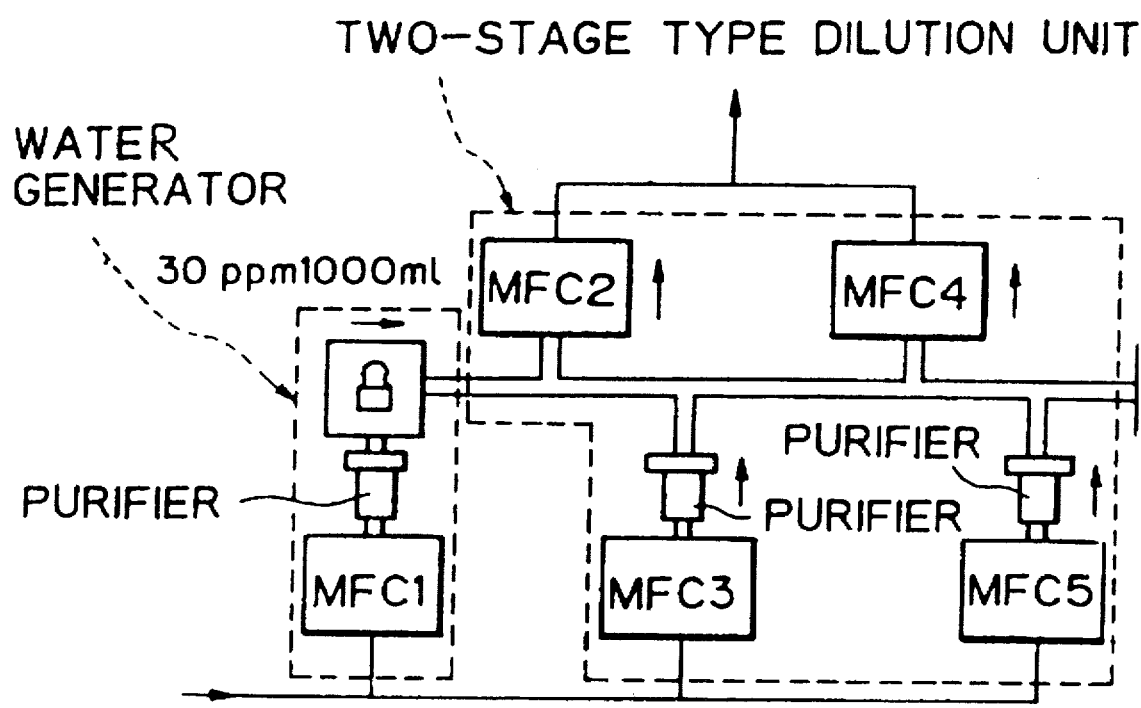
FIG. 14 shows a flow schematic showing standard moisture generator used for measuring the relationships shown in FIGS. 11 and 12.

The cold portions such as the cell 322, the freeze generator 305 and the cold head 305' of the helium refrigerator must be thermally isolated from the ambient air; thus, they are isolated from the ambient air by being enclosed with an airtight chamber 312 that includes the window 324 (made of a light-transmissive material such as glass) and an electrical wiring connector 307, and the chamber 312 is thermally insulated by being evacuated by means of a vacuum system including vacuum valves 325 and 326 and a vacuum pump 328. If the apparatus described above is used to perform a continuous measurement of the points of equilibria, i.e., the subliming point and the point of solidification of the topmost layer, a sensitivity drop will occur on account of the contamination of the mirror surface. This phenomenon is detectable as a change in the slope of the straight line shown in FIG. 5. In such a case, the contamination of the mirror-surface may be reduced by merely heating the chamber to a temperature higher than that of the mirror surface by at least 40°–50° C. The system shown in FIG. 14 is adapted to be capable of a more advantageous approach, i.e., automatic cleaning of the cell with $CO_2$. Shown by 351 is a cylinder filled with liquefied $CO_2$ that has been especially purified to at least 99.999%; 352 is a pressure regulating valve; 353 is a pipe; and 354 is a valve. The $CO_2$ supply mechanism may be connected to the line for supplying the sample gas to be measured; alternatively, it may be a separate mechanism capable of blowing $CO_2$ against the reflector mirror.

Figure 22:
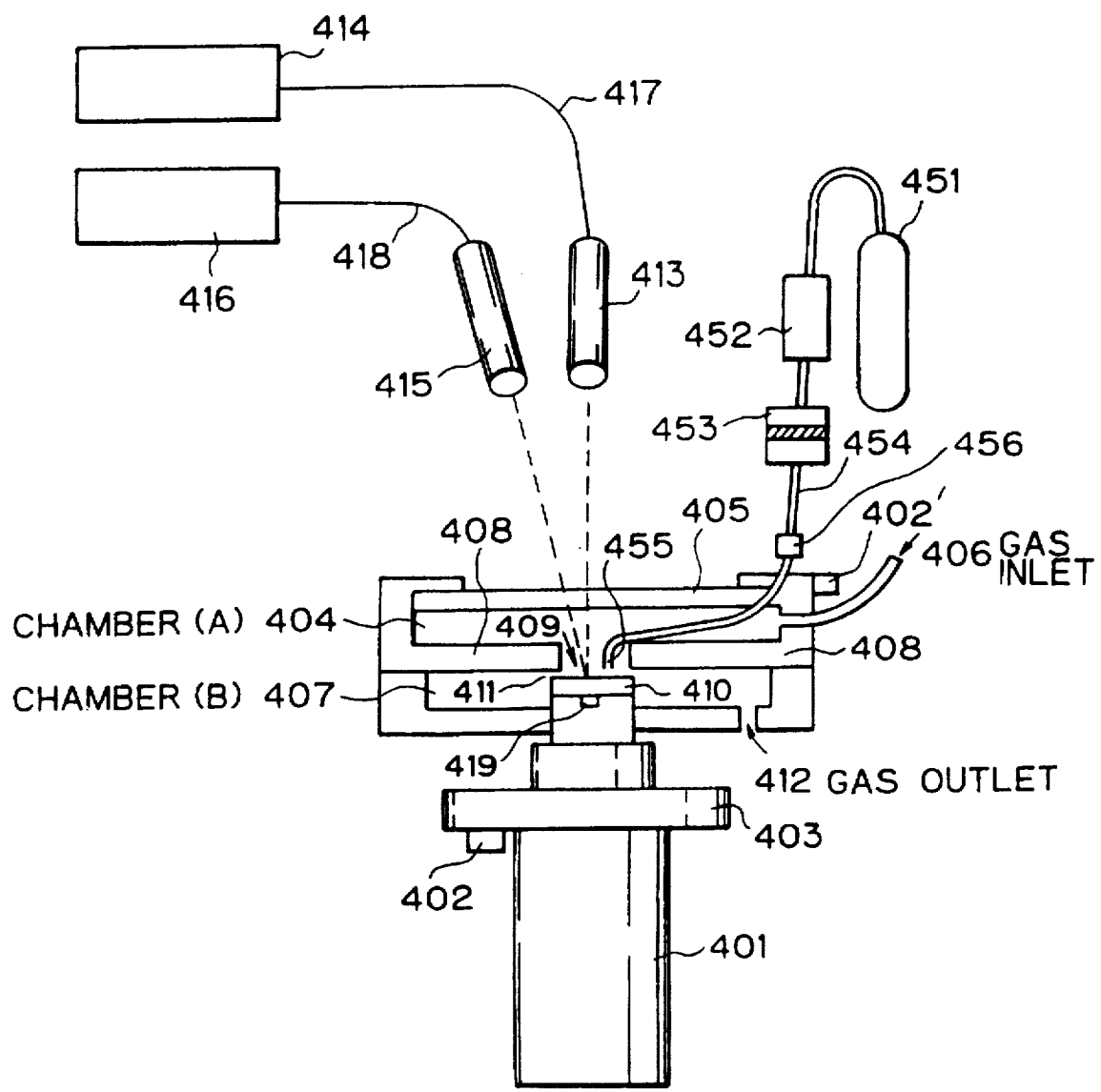
FIG. 22 shows another apparatus preferred for implementing the present invention.

Another embodiment of the present invention is shown in FIG. 22. Shown by 401 is a freeze generator; 402 is a heater; 403 is a cold head; 404 is compartment A which is made of a good heat conductor such as gold, silver, copper, aluminum, silicon, nickel or chromium; 405 is a window made of a light-transmissive material such as glass; 406 is an inlet for supplying a sample gas to be measured; 407 is compartment B, with a hole 409 being formed in the wall 108 at the interface between compartment A 404 and compartment B 107; 410 is a reflector mirror positioned to cover the hole 409; and 411 is the gap between the reflector mirror 410 and the interfacial wall 408. The gap 411 is preferably as small as possible but if it is designed to be extremely small, the slightest manufacturing error can potentially cause the reflector mirror 410 to contact the interfacial wall 408. To avoid this possibility, the gap 411 preferably has a size of 0.1–2.0 mm. At least part of compartment B is made of stainless steel, a Cu-Ni alloy, glass, ceramics or plastics (e.g., a fluorine resin, a polyimide resin and a silicone resin). This is in order to insure that compartment A will not be chilled by the cold head 413. Shown by 412 in FIG. 22 is a gas outlet; 414 is a light source; 413 is a condenser lens; the light source 414 may be an LED emitting at a given wavelength; 415 is a condenser lens; 416 is a photodetector; and 417 and 418 are each an optical fiber.

A measurement of the-water content of a gas with the apparatus shown in FIG. 22 will-proceed as follows. First, the gas to be measured is supplied through the inlet 406 into compartment A 404 which is controlled at a given temperature by means of heater 402'; the gas flows through the hole 409 to make contact with the reflector mirror 410, thereby forming dew or frost on it; the uncondensed gas passes through the gap 411 to be discharged from compartment B through the outlet 412; the gap 411 is small enough to insure that the gas flowing from compartmen A to compartment B through the hole 409 will not fail to contact the reflector mirror 410; the light from the light source 414 is converged by the condenser lens 413 in such a way as to form a beam spot that is focused at the dew or frost layer formed on the reflector mirror 410, and the dew or frost point is determined by the method already described hereinabove.

Shown by 451 in FIG. 22 is a liquefied $CO_2$ cylinder; 452 is a desorption tower for removal of water and oil; 453 is a filter as a dust trap; 454 is a pipe; 455 is a nozzle; and 456 is a pressure regulating valve. The $CO_2$ supply mechanism may be connected to the sample gas supply line 406.

A helium refrigerator (not shown) may typically be used in the freeze generator but other freezing media such as liquefied nitrogen may also be used.

In the apparatus shown in FIG. 22, compartment A preferably has an inner capacity of 0.5–5 $cm^3$. Compartment A may have any shape as seen in plan view.

In FIG. 22, compartment A is shown to be positioned above compartment B. Inversely, compartment B may be positioned above compartment A. If desired, both compartments A and B may be juxtaposed on a horizontal plane.

Figure 23:
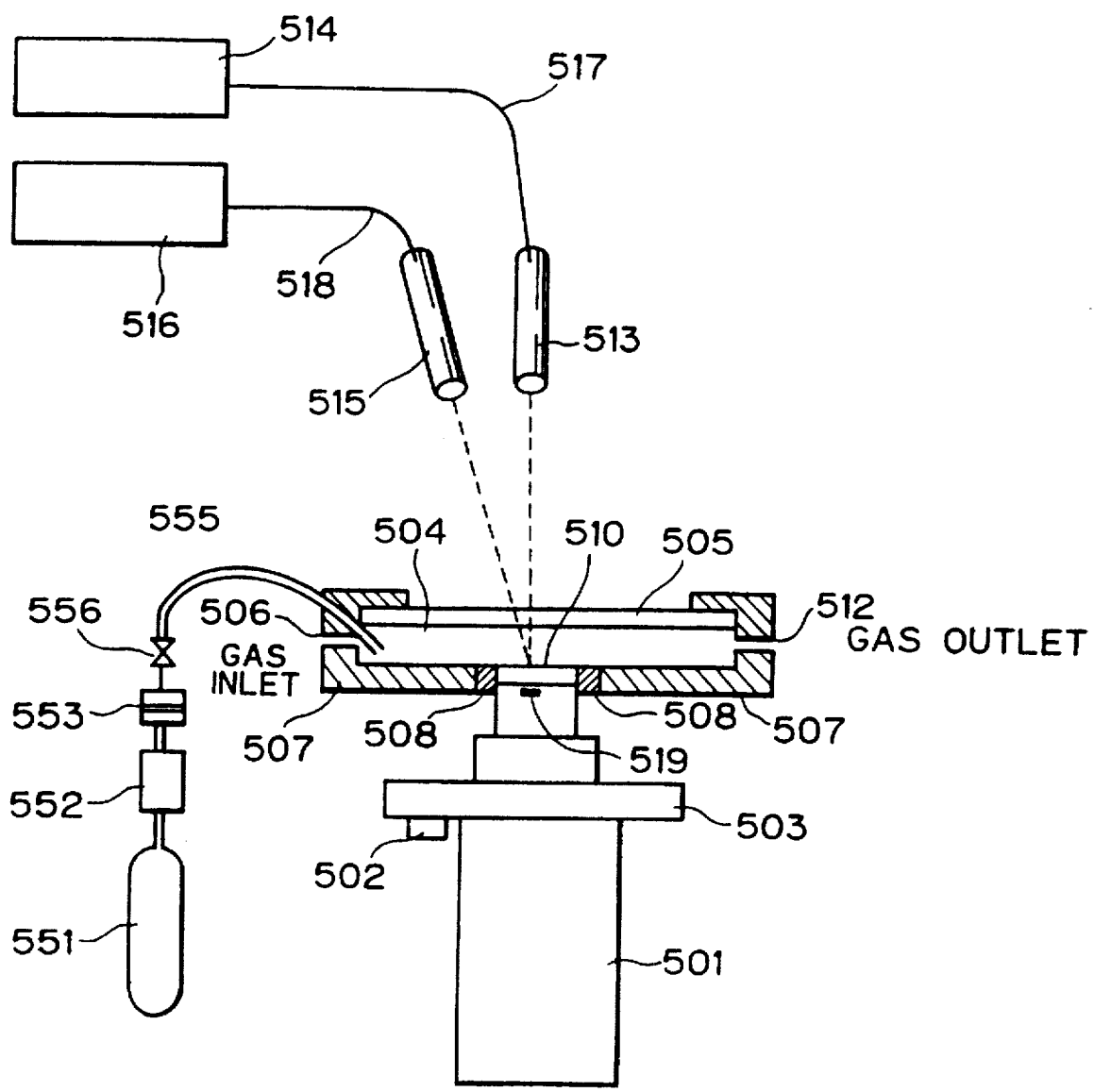
FIG. 23 shows yet another preferred apparatus for impelementing the present invention.

Still another embodiment of the present invention is shown in FIG. 23. Shown by 501 is a freeze generator; 502 is a heater; 503 is a cold head; 504 is a measuring compartment which consists of two parts 507 and 508, with 507 being made of a good heat conductor such a gold, silver, copper, aluminum, silicon, nickel or chromium, and 508 being made of a poor heat conductor such as stainless steel, a Cu—Ni alloy, glass, ceramics or plastics (e.g., a fluorine resin, a polyimide resin and a silicone resin); 505 is a window made of a light-transmissive material such as glass; 506 is an inlet for the sample gas to be measured; 510 is a reflector mirror; 512 is a gas outlet; 513 is a light condenser lens; 514 is a light source such as an LED; 515 is a condenser lens; 516 is a photodetector; and 517 and 518 are each an optical fiber.

A measurement of the water content of a gas with the apparatus shown in FIG. 23 will proceed as follows. First, the gas to be measured is supplied into the measuring compartment 504 through the inlet 506 without cooling it in any particular way, whereupon the gas contacts the reflector mirror 510 to form dew or frost on it; the uncondensed gas will be discharged from the system through the outlet 512; the light from the light source 514 is converged by the condenser lens 513 in such a way as to form a beam spot that is focused at the dew or frost layer formed on the reflector mirror 510, and the dew point or frost point is determined by the method already described hereinabove.

Figure 24:
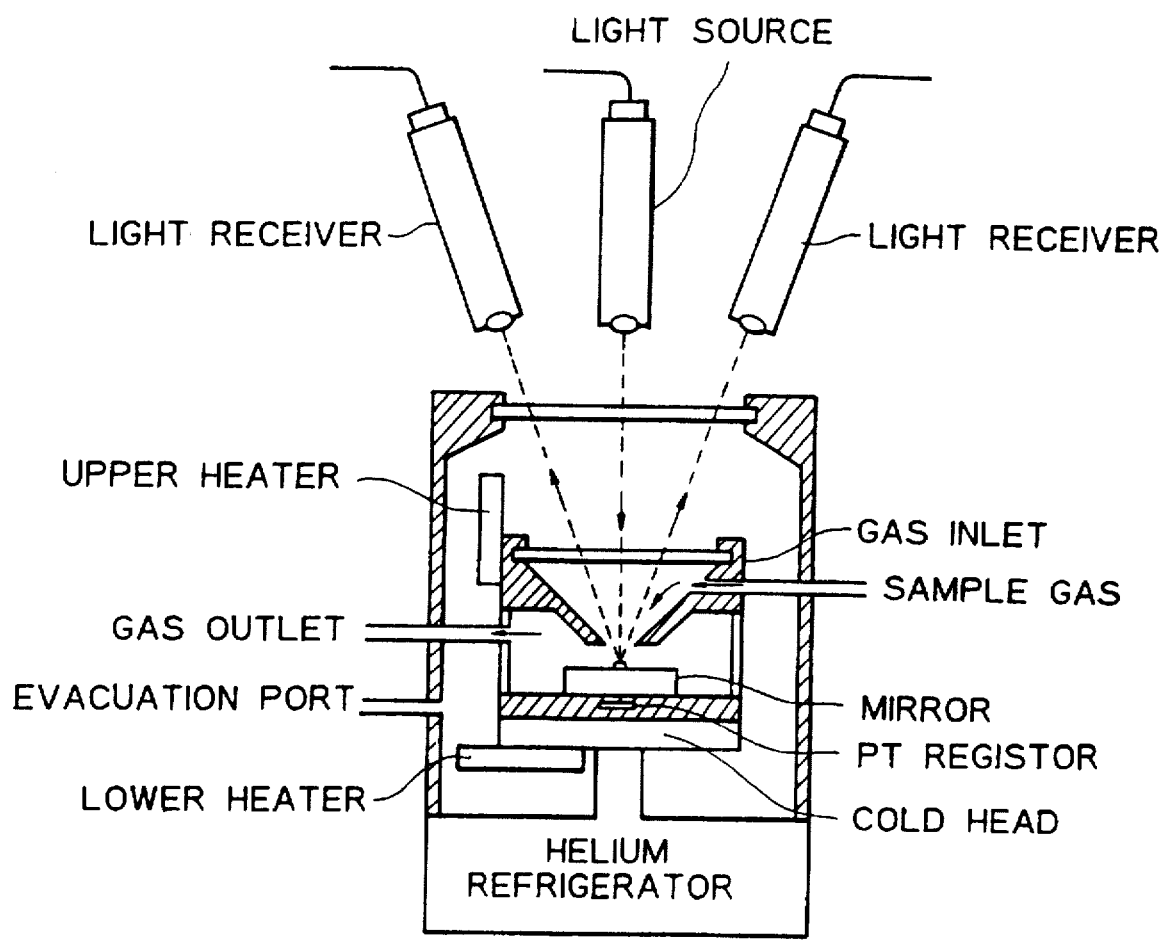
FIG. 24 shows still another apparatus preferred for implementing the present invention.

FIG. 24 shows an apparatus according to yet another embodiment of the present invention, which differs from the embodiment shown in FIG. 22 in that hole 409 is nozzle-shaped and that a higher sensitivity is attained since the scattered light is collected by the detector through condenser lenses provided in two directions.

Figure 25:
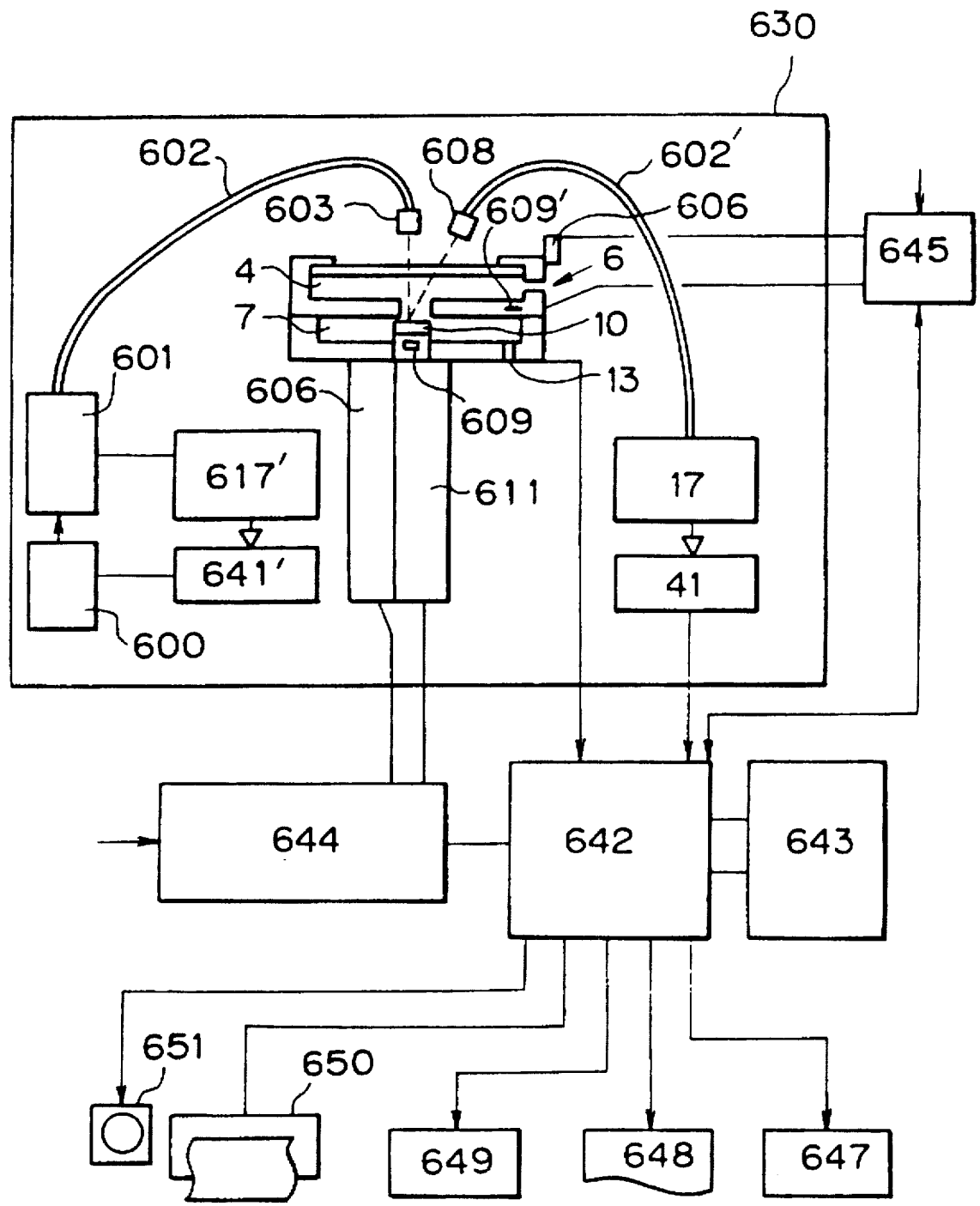
FIG. 25 is a circuit diagram of a photodetector.

FIG. 25 shows another embodiment of the present invention. In this apparatus, the measurement of the dew point or frost point is processed with a computer. The surface of a reflector mirror 10 is cooled with a helium refrigerator 611. In this apparatus, the light from a light-emitting diode 601 travels through an optical fiber 602 to be transmitted to a condenser lens 603, where it is condensed and launched therefrom towards the reflector mirror 10 so that it is focused on its surface. The light is mostly reflected by the mirror 10 but a very small portion of it is scattered and travels through a condenser lens 608 and an optical fiber 602' to be sensed by a photodetector 617.

A sample gas is supplied through a gas inlet 6 into compartment A whose temperature is controlled by a heater 606', a temperature sensor 609' on compartment A and a temperature controller 645. The supplied gas contacts the surface of the reflector mirror 10 and the water present in a very small amount in the gas will be condensed on the mirror surface, whereby the intensity of scattered light from the mirror surface is increased. The uncondensed gas will be released through an outlet 12. The intensified scattered light is collected by the condenser lens 608 and guided through the optical fiber 602' to be sensed by the photodetector 617. The output level of the detector 617 is extremely low, especially in the case where the dew point of the gas to be measured is comparatively low; hence, the output from the photodetector is amplified by an amplifier 641. The output of the amplifier is supplied to a CPU 643 through an interface 642. If the light from the light-emitting diode 601 is noisy, the noise is also amplified by the amplifier 641, producing a signal error. Hence, in order to eliminate the noise, a feedback circuit is provided that is composed of a photodetector 617', an amplifier 641' and a noise eliminator 600. Stated more specifically, part of the light energy from the light-emitting diode 601 is fed to the photodetector 617' which is equivalent to the photodetector 617. The output of the photodetector 617' is further fed for amplification to the amplifier 641' which is equivalent to the amplifier 641 and the amplified output is supplied to the noise eliminator 600. The noise eliminator 600 feeds back a noise-associated output to the light-emitting diode 601, thereby eliminating the noise from its output signal. As a result, only the output due to light scattering can be picked up correctly, thereby lowering the detection limit for dew point. The temperature at the surface of the reflector mirror 10 is detected with the temperature senser 609 and supplied to CPU 643 through the interface 642. The CPU 643 performs calculation on the signal from the temperature sensor 609 indicating the temperature of the mirror surface and on the output from the photodetector 617 and supplies a digital indicator 647, a printer 648, an analog display 650 and a display 649 with output signals that are appropriate for the respective display means. A controller 644 controls the respective elements of the measuring apparatus in various ways. If, for example, the measurement of dew point ends, an electric current for heating with a heater 606 is increased in response to a signal from the controller 644, whereby the dew or frost on the reflector mirror 10 is gradually vaporized at a prescribed heating rate. Conversely, the current to be applied to the heater 606 is reduced so that solidification of water to form dew or frost layers in superposition on the reflector mirror 10 will proceed gradually. If desired, the controller 644 may send a signal to an alarm device 651 which then issues an audible alarm. etc. when the measurement of dew point ends.

Preferably, the surface of the reflector mirror may be composed of a silicon wafer. Silicon wafers as reflector mirrors are excellent in terms of surface smoothness but they have high light absorbance. In order to solve this problem, aluminum is evaporated or sputtered on silicon wafers. However, a reflector mirror in the form of a silicon wafer having an aluminum coat suffers from the problem that its reflectance may drop within a short time. This is because hard and fine alumina or silica particles that are contained in the gas blown through the hole or nozzle, the particles of oxides of Fe, Ni, Cr, Cu, etc. that come out of pipes, and the fine crystals of ice will attach soft metals such as aluminum, thereby making it difficult for the silicon wafer to maintain desired smoothness.

This problem can be solved by covering the thin aluminum coat with a clear and hard aluminum nitride film. In this case, the SN ratio of the apparatus becomes somewhat lower than when only thin Al coat is used (at 633 nm which is the operating wavelength of an LED, the SN ratio was ca. 98%, and at 780 nm which is the operating wavelength of a semiconductor laser, the SN ratio was ca. 93%, with the value for the case of using only the Al coat being taken as 100%); however, the present inventors confirmed that the SN ratio achievable was satisfactorily high and that the reflector mirror could withstand a continued use for at least 10,000 h. A thin AlN film can be formed on the thin Al coat by the following procedure; a silicon wafer that has been fully polished on a (611) or (600) face which is the cleavage face of a silicon crystal is placed in vacuum and aluminum is evaporated on the wafer's surface; or aluminum is sputtered in argon under vacuum; aluminum is further sputtered on the thus formed thin Al film in $N_2$. The thus formed surface of the reflect mirror performed as an ideal protective film for the mirror surface since the thin AlN film was very high and had a high degree of clarity. For an effective measurement, in terms of frost point, of the content of water that is present in a very small amount in a gas having a dew point of −80° C. and below, it is absolutely necessary that condensed light be launched onto the mirror surface at the area against which the sample gas is being blown.

If the sample gas is allowed to contact an extremely cold surface before contact with the reflector mirror, the moisture in the gas will be adsorbed or experience a phase change, thereby causing an incorrect dew point or frost point on the lower side to be erroneously measured. This problem is free from the presention, which permits the temperature of the sample gas to be controlled freely so that the moisture content of the gas can be measured correctly.

Figure 26:
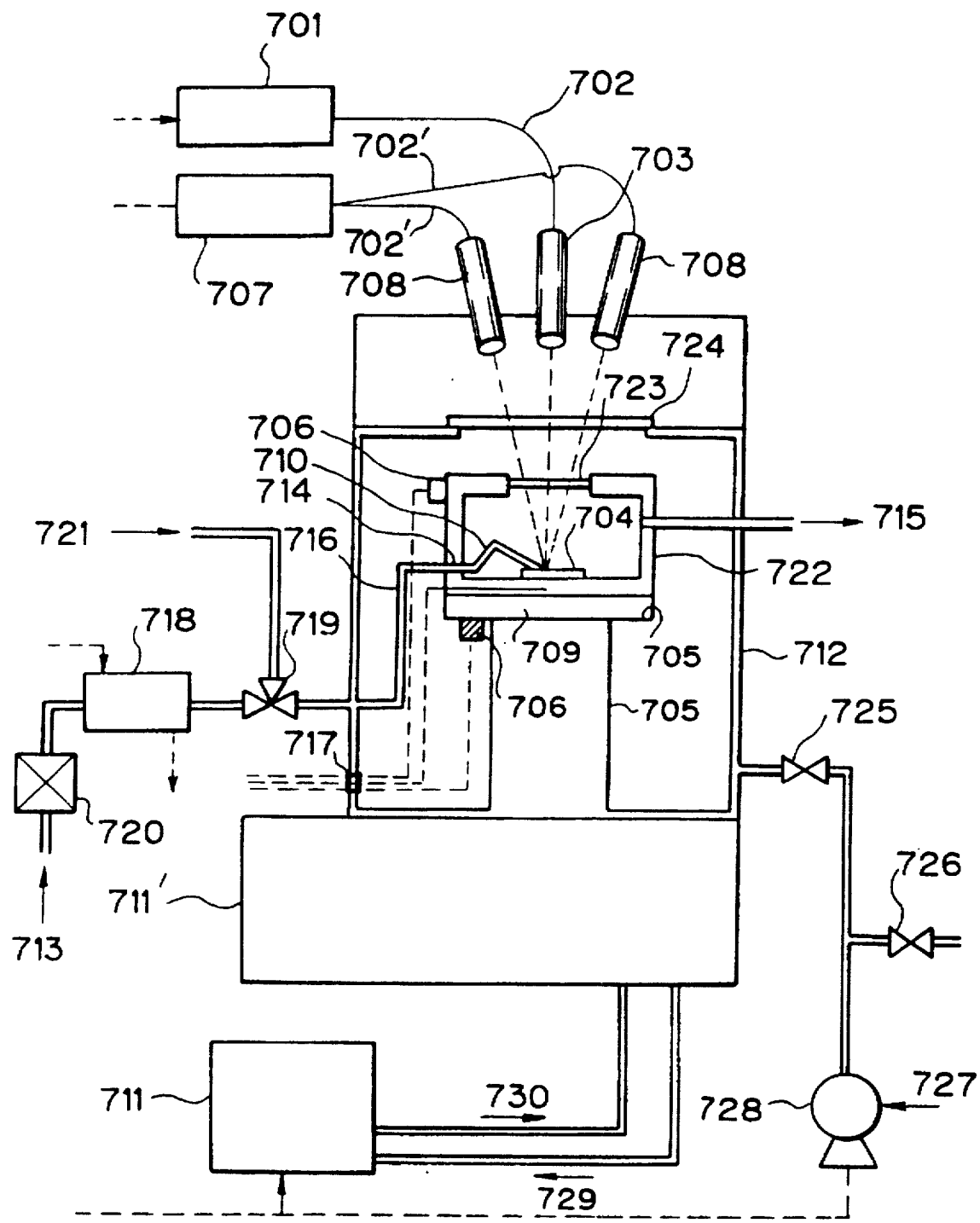
FIG. 26 is a flowsheet for an apparatus according to preferred embodiment of the present invention.

FIG. 26 illustrates an embodiment of the present invention. A helium refrigerator is used in the cooling system and a helium gas as compressed with a circulating helium compressor 711 is circulated through a loop consisting of a line 730, a drive mechanism 711', a freeze generator 705, the drive mechanism 711' and a line 729. The freeze generator 705 comprises a piston or displacer inserted into a stainless steel cylinder and by driving the piston or displacer vertically by means of the drive mechanism 711', freeze is generated on the cold head 705' at the upper end of the cylinder 705. A metallic cell (hereafter referred to simply as the "cell") 722 with a built-in mirror 704 is disposed in such a way as to insure adequate thermal contact with the cold head 705'. The cell 722 is partly formed of a light-transmissive material 723 such as glass. The reflector mirror 704 in the form of a smooth-surfaced silicon wafer is placed on the bottom of the cell 722 in such a way as to insure adequate thermal contact. A temperature sensor 709 such as a thermocouple or a resistance thermometer is inserted into the bottom wall of the cell 722.

A sample gas to be measured for dew point is fed into the apparatus through a gas inlet 713, passes through a filter 720, has its flow rate adjusted to be constant by means of an automatic flow adjusting device 718 such as a mass flow controller, and is controlled in flow direction by a three-way valve 719 to be discharged from the system through a gas outlet 721. The sample gas line will reach an equilibrium faster when the volume of gas purge is high than when it is low. The sample gas then flows into the cell 722 via a gas line 716. In the cell 722, the gas is blown against the reflector mirror 704 and is thereafter discharged from the cell 722 through a gas outlet 715. To increse the response speed, the gas line starting from inlet 713 and extending up to part 710 is desirably composed of a tube of SUS 316L that has a diameter of ¼", ⅛", ¹⁄₁₆", etc., that has been electropolished or otherwise treated to provide a smooth inner surface, and that has been heat treated by passivation with an ultrapure inert gas such as a gas with a moisture content of less than 5 ppb.

The light from a light-emitting diode (LED) 701 is guided through an optical fiber 702 to become partly convergent and is further focused to form a beam spot that passes through windows 724 and 723 made of a light-transmissive material to be incident normally on the surface of the reflector mirror 704. To determine the point of dew or frost condensation on the surface of the reflector mirror, the light scattered from it is collected by condenser lenses 708 and 708' positioned in directions exterior to the angle of reflection of the light projected from the lens 703, and the collected light is guided through an optical fiber 702' and detected with a PN photodiode 707, the point of dew or frost condensation is finally evaluated on the basis of the change in the intensity of scattered light as measured with the PN photodiode 707. The temperature corresponding to that point is measured with the temperature sensor 709.

The cold portions such as the cell 722, the freeze generator 705 and the cold head 705' of the helium refrigerator must be thermally isolated from the ambient air; thus, they are isolated from the ambient air by being enclosed with an airtight chamber 712 that includes the window 724 (made of a light-transmissive material such as glass) and an electrical wiring connector 707, and the chamber 712 is thermally insulated by being evacuated by means of a vacuum system including vacuum valves 725 and 726 and a vacuum pump 728.

Figure 27:
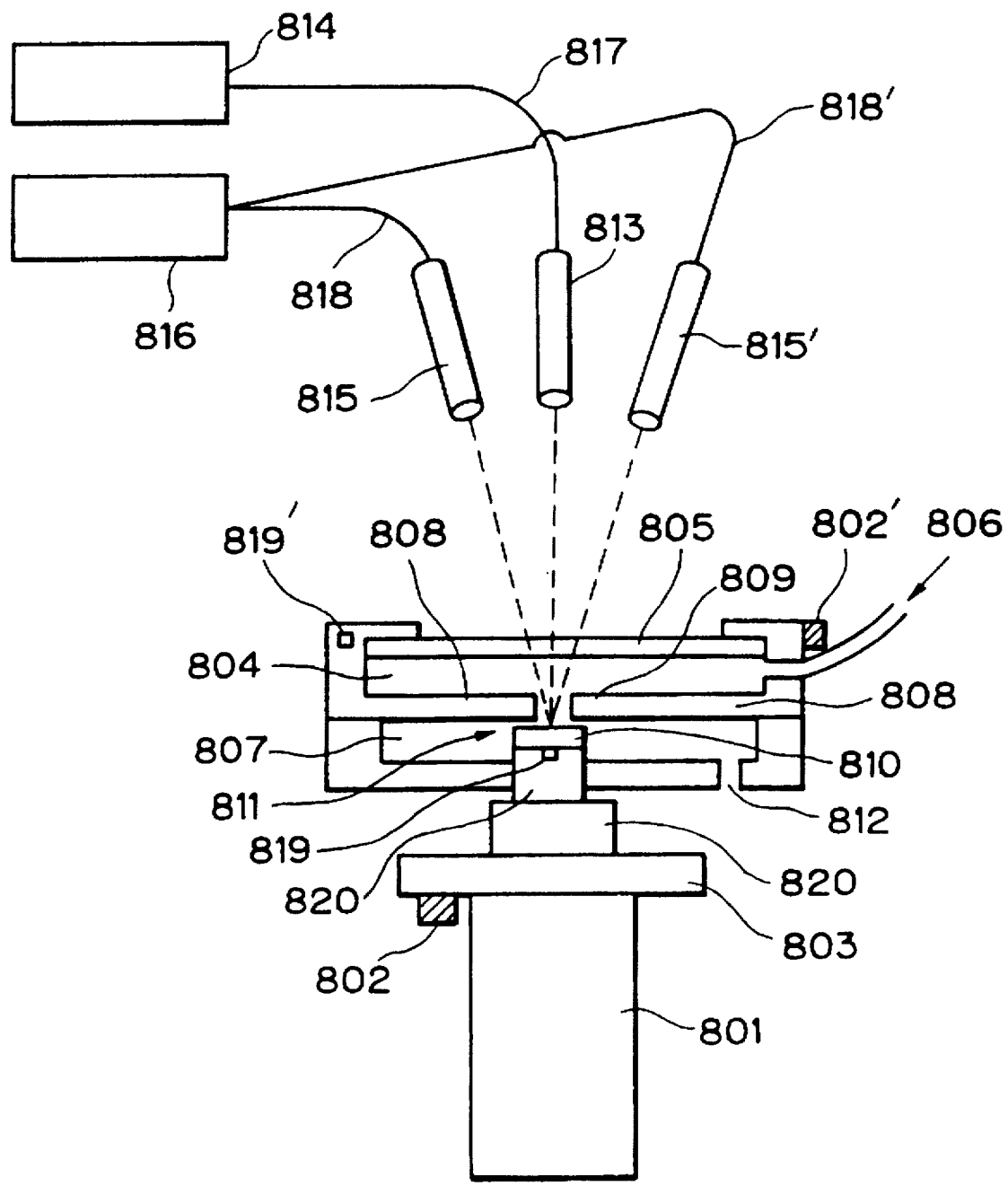
FIG. 27 is a flowsheet for an apparatus according to another preferred embodiment of the present invention.

Another embodiment of the present invention is shown in FIG. 27. Shown by 801 is a freeze generator; 802 and 802' are each a heater; 803 is a cold head; 804 is compartment A which is made of a good heat conductor such as gold, silver, copper, aluminum, silicon, nickel or chromium; 805 is a window made of a light-transmissive material such as glass; 806 is an inlet for supplying a sample gas to be measured; 807 is compartment B, with a hole 809 being formed in the wall 808 at the interface between compartment A 804 and compartment B 807; 810 is a reflector mirror positioned on a heat conductor 820 to cover the hole 809; the heat conductor 820 is a metal having the highest possible heat conductivity such as Au, Ag, Cu, Al, Si, Ni or Cr; and 811 is the gap between the reflector mirror 810 and the interfacial wall 808. The gap 811 is preferably as small as possible but if it is designed to be extremely small, the slightest manufacturing error can potentially cause the reflector mirror 810 to contact the interfacial wall 808. To avoid this possibility, the gap 811 preferably has a size of 0.1–2.0 mm. At least part of compartment B is made of stainless steel, a Cu-Ni alloy, glass, ceramics or plastics (e.g., a fluorine resin, a polyimide resin and a silicone resin). This is in order to insure that compartment A will not be chilled by the cold head 803. Shown by 812 in FIG. 27 is a gas outlet; 814 is a light source; 813 is a condenser lens; the light source 814 may be an LED emitting at a given wavelength; 815 and 815' are each a condenser lens; 816 is a photodetector; and 817, 818 and 818' are each an optical fiber.

A measurement of the water content of a gas with the apparatus shown in FIG. 27 will proceed as follows. First, the gas to be measured is supplied through the inlet 806 into compartment A 804 which is controlled at a given temperature by means of heater 802'; the gas flows through the hole 809 to make contact with the reflector mirror 810, and the water present in a very small amount in the gas will form dew or frost on the reflector mirror 810. The uncondensed gas passes through the gap 811 to be discharged from compartment B through the outlet 812; the gap 811 is small enough to insure that the gas flowing from compartment A to compartment B through the hole 809 will not fail to contact the reflector mirror 810; the light from the light source 814 is converged by the condenser lens 813 in such a way as to form a beam spot that is focused at the dew or frost layer formed on the reflector mirror 810, and the dew point or frost point is evaluated by measuring the change in the intensity of scattered light due to dew or frost with the condenser lenses 815 and 815' and the detector 816. The temperature corresponding to that point is measured with the temperature sensor 819. The temperature of the reflector mirror is controlled by means of the temperature sensor 819 and the heater 802, whereas the temperature in compartment A is controlled by means of the temperature sensor 819' and the heater 802'.

In the present invention, at least two units of the light-receiving device are employed but the number of PN photodiodes to be used may be one. In this case, each light-receiving unit is connected TO the PN photodiode by an optical fiber. The light-receiving units are preferably mounted at angles of 30–90 degrees with respect to the optical axis of the projecting light.

The apparatuses shown in FIGS. 15–20 are preferable. The apparatus shown in FIG. 19 does not have two or more condenser lenses. The apparatus, which is shown in FIG. 19, equipped with two or more condenser lenses is most preferable.

The standard gas capable of creating a desired water content for use in the experiment on determining the water content by measurements of the points of equilibria was generated by diluting a 10-ppm standard gas with the apparatus shown in FIG. 18, which is commercially available from Hitachi Tokyo Electronics Co., Ltd. Symbol "MFC" used in FIG. 28 stands for a "mass flow controller".

Figure 28:
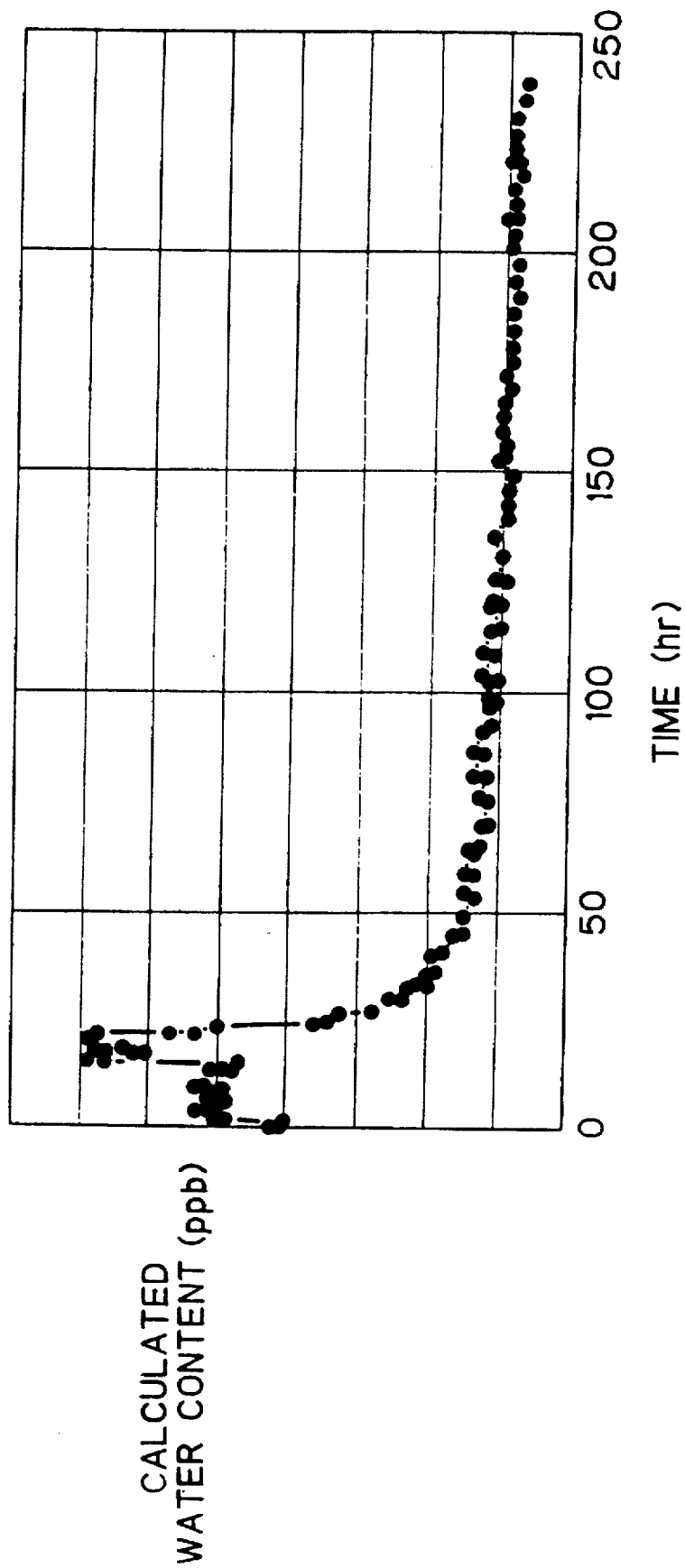
FIG. 28 is a graph plotting the values obtained by a continuous measurement on the flow of a standard gas.

FIG. 28 is a graph showing the result of an experiment in which the water content of a gas was measured by allowing it to flow through a dew point meter for a prolonged time after it had been passed through a SAES Getter Purifier (SAES Getters S.p.A.) using a zirconium alloy capable of removing impurities at an elevated temperature of 400° C. In the initial period, the gas was not passed through the water removing device. After passage through the Getter Purifier, the water content of the gas dropped to 1 ppb and leveled off near at this value for more than 200 h. This shows that the method of the present invention enables the dew point or frost point to be measured in a consistent way to yield stable values over an extended period of time.

PREFERABLE EMBODIMENT

EXAMPLE 1

The case where the temperature of compartment or cell A was adjusted at 20° C. (the invention) and the case where the cell temperature was adjusted at −100° C. were compared with respect to the dew point where nucleus formation occurred. The results are shown below. The results of experiments conducted at cell temperatures of 0° C. and 30° C. were almost the same as the result for 20° C. It was therefore clear that cooling cell A to a low temperatrure as low as −100° C. could cause supercooling on account of the adsorption of water in cell A.

| Sample | 1 | 2 | 3 | 4 |
|---|---|---|---|---|
| Prior art | −107.4° C. | −108.3° C. | −119.8° C. | not detected |
| Invention | −98.6° C. | −99.7° C. | −111.2° C. | −119.7° C. |
| Difference | 8.8° C. | 8.6° C. | 8.6° C. | |

EXAMPLE 2

The case where the temperature of cell A was adjusted at 20° C. and the case where the cell temperature was adjusted at −50° C. were compared with respect to the frost point. The results were −112.5° C. and −110.5° C. in the respective cases, with the value in the case of −50° C. being higher by 2° C. It was therefore clear that preliminary cooling cell a to ca. −50° C. resulted in the highest dew point (nucleus forming frost point).

EXAMPLE 3

Measurement of the subliming point were conducted with the temperature of cell A adjusted at 20° C., −10° C. or −50° C. and the results were −105.0° C., 104.3° C. and −104.7° C., respectively. It was therefore clear that the subliming point or the point of solidification of the topmost layer was little dependent on the temperature of cell A.

The apparatus of the present invention is characterized by providing at least two units of the light-receiving device and as long as this condition is met, the actual system may be other than the three embodiments described above.

Using at least two units of the light-receiving device in accordance with the present invention helps attain the following advantages;
(a) Sensitivity is increased by a factor proportional to the number of detectors used;
(b) Detection is possible even if the position of frost condensation varies slightly; and
(c) In the absence of the need to perform precise adjustments of the optical axis, the apparatus is simple to use.

We claim:
1. An apparatus for determining the frost point of a gas containing a very small amount of water comprising:
 (1) compartment A made of a good heat conductor;
 (ii) an inlet for the gas to be measured, which inlet is provided on compartment A;
 (iii) a heater for adjusting the temperature in compartment A, and a temperature sensor;
 (iv) compartment B provided adjacent to compartment A, at least part of compartment B being made of a poor heat conductor;
 (v) a hole provided at the interface between compartments A and B;
 (vi) a reflector mirror having a temperature sensor, said reflector mirror being provided on compartment B in such a way as to cover the hole, and said mirror being connected thermally to a freeze source in such a way that it can be varied from room temperature to at least −80° C.;
 (vii) a gas outlet provided on compartment B;
 (viii) a small gap formed between said hole and said reflector mirror;
 (ix) a device that allows convergent rays of light or laser light to be emitted onto the surface of the reflector mirror;
 (x) a photodetector equipped with a condenser lens which condenser lens condenses scattered rays of light or reflected rays of light from frost formed on the surface of the reflector mirror when said gas to be measured contacts said mirror and said water in said gas condenses as frost and which photodetector permits the detection of change in the intensity of the condensed light; and
 (xi) a detector device that senses the temperature at which condensation of frost occurs on the reflector mirror when said condensation of frost is determined based on the change in the intensity of the condensed light.

2. An apparatus for determining the frost point of a gas containing a very small amount of water wherein said apparatus comprises
 (a) a reflector mirror;
 (b) means to vary the temperature of said reflector mirror from room temperature to at least −80° C.;
 (c) means for sensing the temperature of said reflector mirror;
 (d) means for contacting said reflector mirror with the gas to be measured;
 (e) means of irradiating said reflector mirror with light selected from the group consisting of focused rays of light and laser light;
 (f) means for detecting the change in the intensity of scattered light or reflected light coming from said reflector mirror when condensation of frost occurs on said reflector mirror, and (g) means for determining the frost point of the gas as the temperature of said reflector mirror when said change in the intensity of the scattered light or reflected light is detected;
wherein said means for contacting said reflector mirror with gas to be measured comprises
 (i) compartment A made of a good heat conductor;
 (ii) an inlet for the gas to be measured, which inlet is provided on compartment A;
 (iii) compartment B provided adjacent to compartment A, at least part or compartment B being made of a poor heat conductor;
 (iv) a hole provided at the interface between compartments A and B;
 (v) a small gap formed between said hole and said reflector mirror; and
wherein said reflector mirror is provided on compartment B in such a way as to face and cover said hole.

* * * * *

UNITED STATES PATENT AND TRADEMARK OFFICE
CERTIFICATE OF CORRECTION

PATENT NO. : 5,615,954
DATED : April 1, 1997
INVENTOR(S) : NISHIZAWA et al.

It is certified that error appears in the above-indentified patent and that said Letters Patent is hereby corrected as shown below:

On the title page, item [62], after "1994", delete "abandoned" and insert --Pat. No. 5,482,371--.

Signed and Sealed this

Thirtieth Day of September, 1997

Attest:

BRUCE LEHMAN

Attesting Officer

Commissioner of Patents and Trademarks